United States Patent
Wilke et al.

(10) Patent No.: US 9,463,020 B2
(45) Date of Patent: *Oct. 11, 2016

(54) WOUND CLOSURE PRODUCT

(71) Applicant: Wound Care Technologies, Inc., Chanhassen, MN (US)

(72) Inventors: Robert C. Wilke, Eden Prairie, MN (US); Daniel M. Elliott, Shorewood, MN (US); George M. Hoedeman, Eden Prairie, MN (US); John J. Berkey, Buffalo, MN (US); Paul J. Anderson, Eden Prairie, MN (US)

(73) Assignee: Wound Care Technologies, Inc., Chanhassen, MN (US)

( * ) Notice: Subject to any disclaimer, the term of this patent is extended or adjusted under 35 U.S.C. 154(b) by 357 days.

This patent is subject to a terminal disclaimer.

(21) Appl. No.: 13/925,221

(22) Filed: Jun. 24, 2013

(65) Prior Publication Data

US 2014/0088643 A1    Mar. 27, 2014

Related U.S. Application Data

(63) Continuation of application No. 13/149,084, filed on May 31, 2011, now Pat. No. 8,469,997, which is a continuation of application No. 12/217,513, filed on Jul. 3, 2008, now Pat. No. 7,972,362, which is a continuation of application No. 10/949,115, filed on Sep. 13, 2004, now Pat. No. 7,455,681.

(51) Int. Cl.
*A61B 17/08* (2006.01)
*A61D 1/00* (2006.01)
(Continued)

(52) U.S. Cl.
CPC ......... *A61B 17/083* (2013.01); *A61B 17/0466* (2013.01); *A61B 17/08* (2013.01);
(Continued)

(58) Field of Classification Search
CPC A61B 17/08; A61B 17/083; A61B 17/0466; A61B 2017/086; A61B 2017/0495; A61B 2017/0496
See application file for complete search history.

(56) References Cited

U.S. PATENT DOCUMENTS

| 114,750 A | 5/1871 | Battersby |
|---|---|---|
| 363,538 A | 5/1887 | Penny |

(Continued)

FOREIGN PATENT DOCUMENTS

| EP | 0 531 742 A1 | 3/1993 |
|---|---|---|
| FR | 2 268 504 | 11/1975 |

(Continued)

OTHER PUBLICATIONS

CANICA® design brochure, "Canica Wound Closure System," © Canica Design, 2004 (5 pages).

(Continued)

*Primary Examiner* — Melanie Tyson
(74) *Attorney, Agent, or Firm* — Merchant & Gould P.C.

(57) ABSTRACT

A wound closure system and a method of closing a wound are disclosed. The wound closure system includes a plurality of skin anchors mechanically attached to external skin tissue around a periphery of a wound, a line extending between the skin anchors, the line slidably engaged with each skin anchor, and a biasing member that provides tension on the line to draw all of the skin anchors toward the wound. The method of closing a wound includes the steps of attaching a plurality of skin anchors to external skin around a periphery of a wound, extending a line between the skin anchors around substantially the entire periphery of the wound, and providing tension to the line to draw the skin anchors toward the wound.

20 Claims, 25 Drawing Sheets

(51) Int. Cl.
*A61B 17/04* (2006.01)
*A61M 1/00* (2006.01)
*A61B 17/11* (2006.01)

(52) U.S. Cl.
CPC .......... *A61B 90/02* (2016.02); *A61M 1/0088* (2013.01); *A61B 2017/0496* (2013.01); *A61B 2017/1142* (2013.01)

(56) References Cited

U.S. PATENT DOCUMENTS

| | | |
|---|---|---|
| 2,421,193 A | 5/1947 | Gardner |
| 3,402,716 A | 9/1968 | Baxter |
| 3,559,652 A | 2/1971 | Banitt et al. |
| 3,650,274 A | 3/1972 | Edwards et al. |
| 3,825,010 A | 7/1974 | McDonald |
| 4,646,731 A | 3/1987 | Brower |
| 4,742,826 A | 5/1988 | McLorg |
| 4,825,866 A | 5/1989 | Pierce |
| 5,127,412 A | 7/1992 | Cosmetto et al. |
| 5,234,462 A | 8/1993 | Pavletic |
| 5,330,489 A | 7/1994 | Green et al. |
| 5,356,412 A | 10/1994 | Golds et al. |
| 5,462,542 A | 10/1995 | Alesi, Jr. |
| 5,507,775 A | 4/1996 | Ger et al. |
| 5,556,428 A | 9/1996 | Shah |
| 5,618,310 A | 4/1997 | Ger et al. |
| 5,649,960 A | 7/1997 | Pavletic |
| 5,769,893 A | 6/1998 | Shah |
| 5,843,123 A | 12/1998 | Brazeau |
| 5,968,097 A | 10/1999 | Frechet et al. |
| 5,980,473 A | 11/1999 | Korakianitis et al. |
| 6,120,525 A | 9/2000 | Westcott |
| 6,241,747 B1 | 6/2001 | Ruff |
| 6,254,624 B1 | 7/2001 | Oddsen et al. |
| 6,471,715 B1 | 10/2002 | Weiss |
| 6,599,310 B2 | 7/2003 | Leung et al. |
| 6,613,059 B2 | 9/2003 | Schaller et al. |
| 6,694,643 B1 * | 2/2004 | Hsu .......................... A43C 1/00 24/712.1 |
| 6,960,221 B2 | 11/2005 | Ho et al. |
| 7,056,331 B2 | 6/2006 | Kaplan et al. |
| 7,455,681 B2 * | 11/2008 | Wilke ................ A61B 17/0466 606/216 |
| 7,686,829 B2 * | 3/2010 | Elliott .................... A61B 17/08 606/216 |
| 7,927,352 B2 * | 4/2011 | Wilke ................ A61B 17/0466 606/216 |
| 7,972,362 B2 * | 7/2011 | Wilke ................ A61B 17/0466 606/216 |
| 8,469,997 B2 * | 6/2013 | Wilke ................ A61B 17/0466 606/216 |
| 2001/0018592 A1 | 8/2001 | Schaller et al. |
| 2001/0047181 A1 | 11/2001 | Ho et al. |
| 2003/0092969 A1 | 5/2003 | O'Malley et al. |
| 2003/0149447 A1 | 8/2003 | Morency et al. |
| 2003/0163160 A1 * | 8/2003 | O'Malley .............. A61B 17/08 606/213 |
| 2005/0131430 A1 | 6/2005 | Ravidumar |
| 2005/0192599 A1 | 9/2005 | Demarias |
| 2006/0058842 A1 | 3/2006 | Wilke et al. |
| 2006/0095076 A1 | 5/2006 | Elliott et al. |
| 2008/0097483 A1 | 4/2008 | Ortiz et al. |
| 2009/0018578 A1 | 1/2009 | Wilke et al. |
| 2009/0018579 A1 | 1/2009 | Wilke et al. |
| 2010/0185236 A1 | 7/2010 | Elliott et al. |

FOREIGN PATENT DOCUMENTS

| | | |
|---|---|---|
| WO | WO 95/28886 | 11/1995 |
| WO | WO 99/35974 | 7/1999 |
| WO | WO 2005/002452 | 1/2005 |
| WO | WO 2005/016153 A1 | 2/2005 |

OTHER PUBLICATIONS

Progressive Surgical Products Inc. brochure, "External Tissue Expansion," PROXIDERM™, Copyright 1997 (3 pages).

"History of Wound Care," http://www.proxiderm.com/html/intro2.html, 3 pages (date printed: Jul. 28, 2004).

"Proxiderm Procedure," http://www.proxiderm.com/html/intro3.html, 2 pages (date printed: Jul. 28, 2004).

Schessel, Eli S. et al., "External Constant Tension Expansion of Soft Tissue for the Treatment of Ulceration of the Foot and Ankle," *The Journal of Foot & Ankle Surgery*, vol. 39, No. 5, pp. 321-328, Sep./Oct. 2000.

Topical Hyperbaric Oxygen™ Therapy, "Healing Difficult Wounds," http://www.gwrmedical.com, 3 pages (date printed: Apr. 28, 2004).

Prosecution History of U.S. Appl. No. 10/982,509 (OA Nov. 14, 2007; Resp Feb. 14, 2008).

Galil, K. et al., "Effect of N-Butyl-2-Cyanoacrylate (Histoacryl Blue) on the Healing of Skin Wounds," *J. Canad. Dent. Assn.*, No. 7, pp. 565-569 (1984).

Gibson, T. et al., "Directional Variation in Extensibility of Human Skin in Vivo," *J. Biomechanics*, vol. 2, pp. 201-204 (1969).

Gibson, T. et al., "The Mobile Micro-Architecture of Dermal Collagen," *Brit. J. Surg. . . .*, vol. 52, No. 10, pp. 764-770 (Oct. 1965).

Hirshowitz, B. et al., "A Skin-Stretching Device for the Harnessing of the Viscoelastic Properties of Skin," *Plastic and Reconstructive Surgery*, vol. 92 No. 2, pp. 260-270 (Aug. 1993).

Ling, M. et al., "Presuturing—A New Technique for Closing Large Skin Defects: Clinical and Experimental Studies," *Plastic and Reconstructive Surgery*, vol. 81, No. 5, pp. 694-702 (May 1988).

Mustoe, T. et al., "Physical, Biomechanical, Histologic, and Biochemical Effects of Rapid versus Conventional Tissue Expansion," *Plastic and Reconstructive Surgery*, vol. 83, No. 4, pp. 687-691 (Apr. 1989).

Radovan, C., "Tissue Expansion in Soft-Tissue Reconstruction," *Plastic and Reconstructive Surgery*, vol. 74, No. 4, pp. 482-490 (Oct. 1984).

Stark, H. et al., "Directional Variations in the Extensibility of Human Skin," *British Journal of Plastic Surgery*, vol. 30, pp. 105-114 (1977).

* cited by examiner

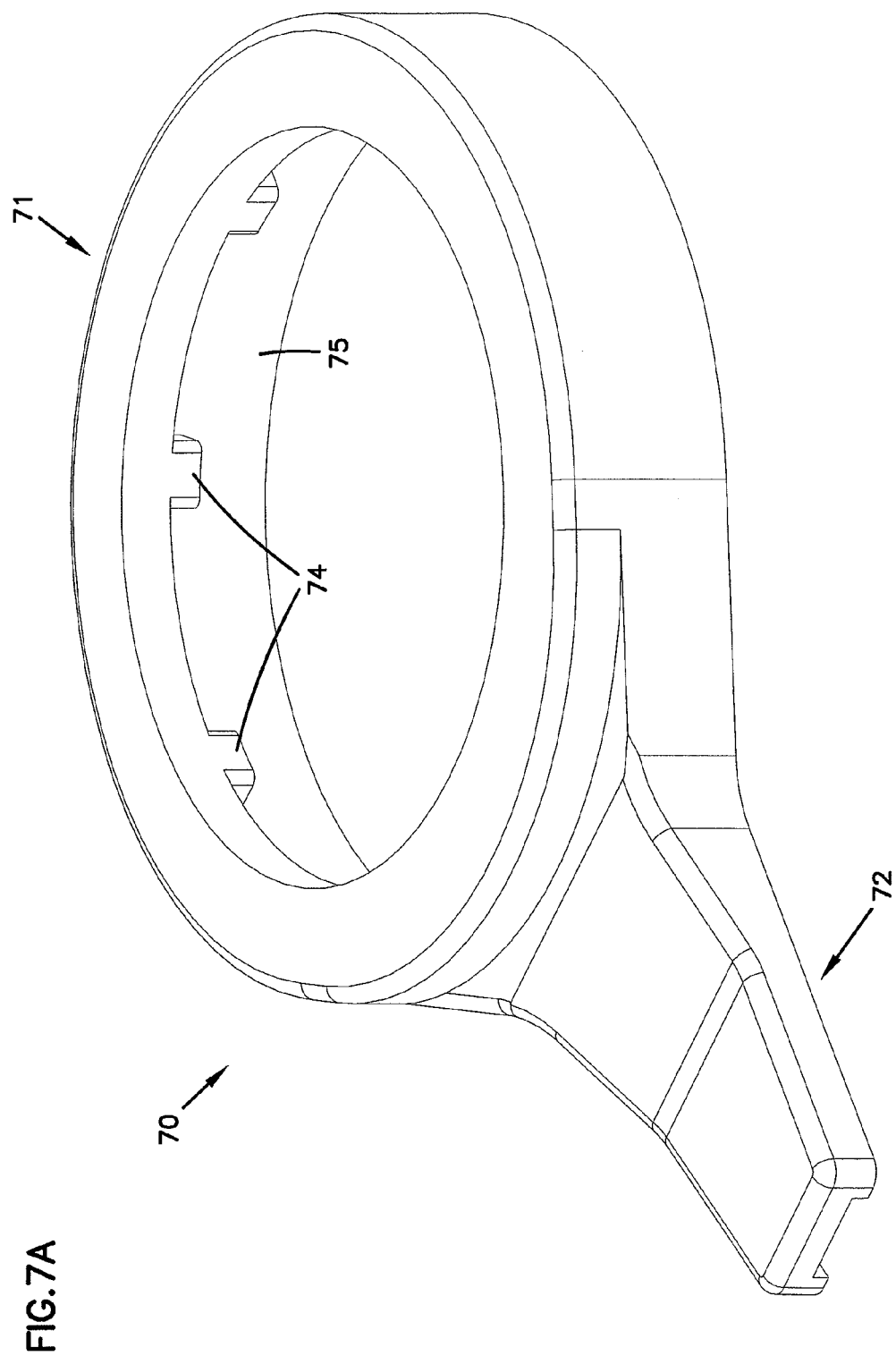

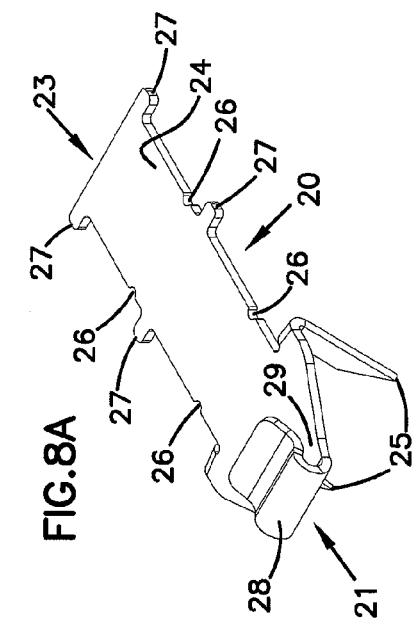
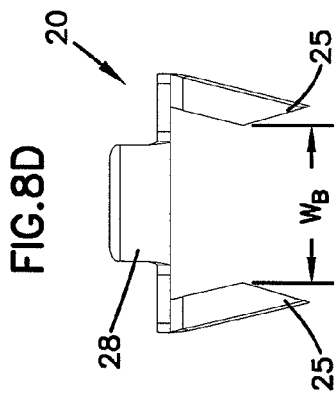
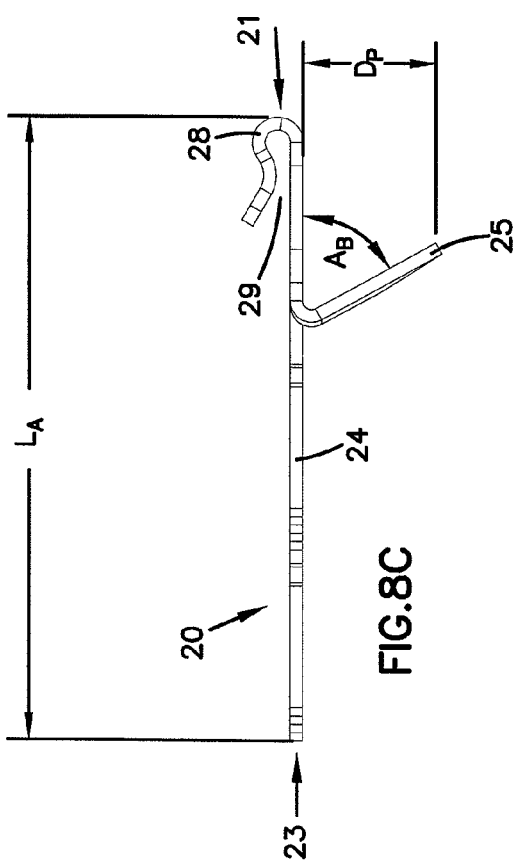
FIG.8A
FIG.8D
FIG.8B
FIG.8C

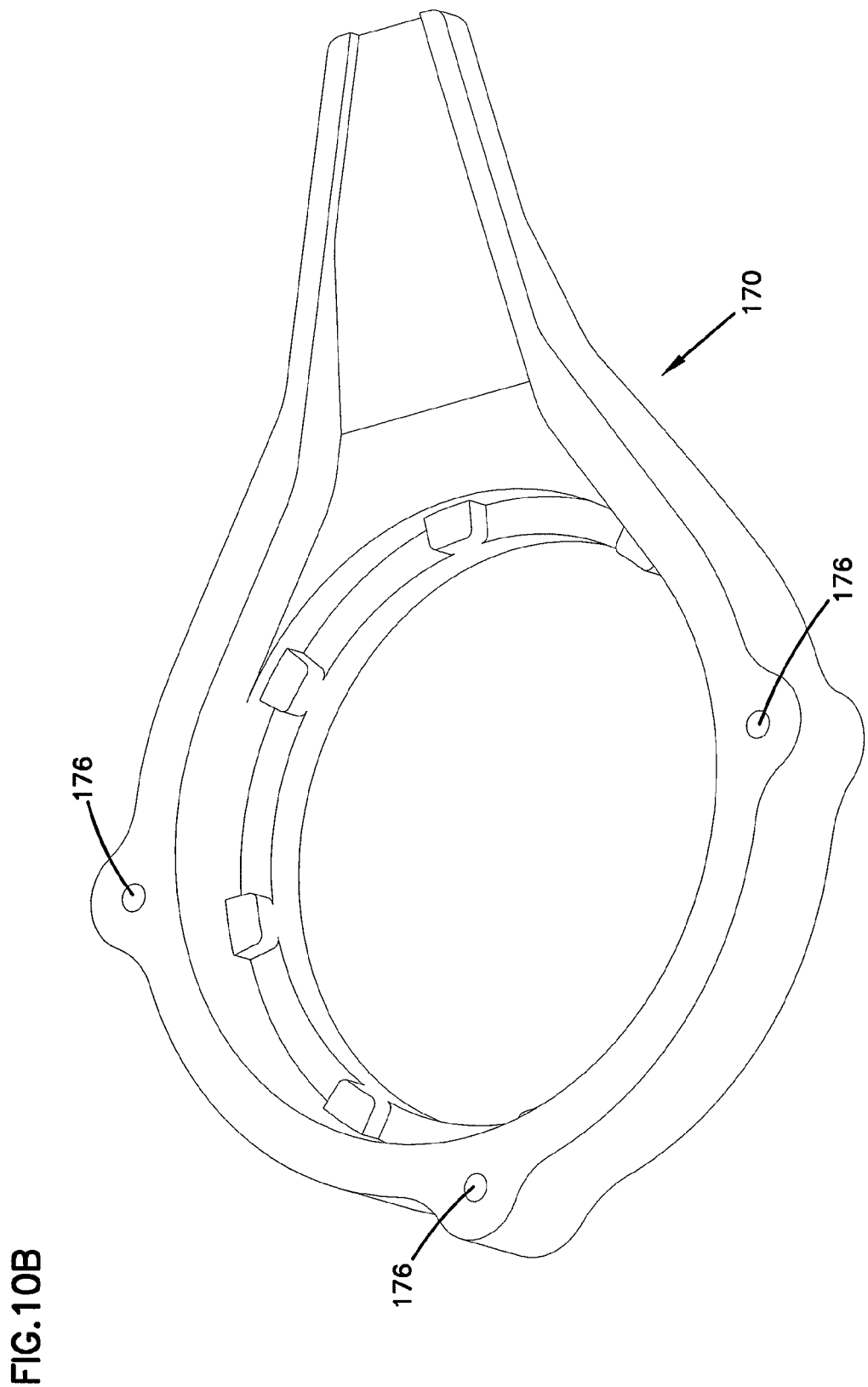

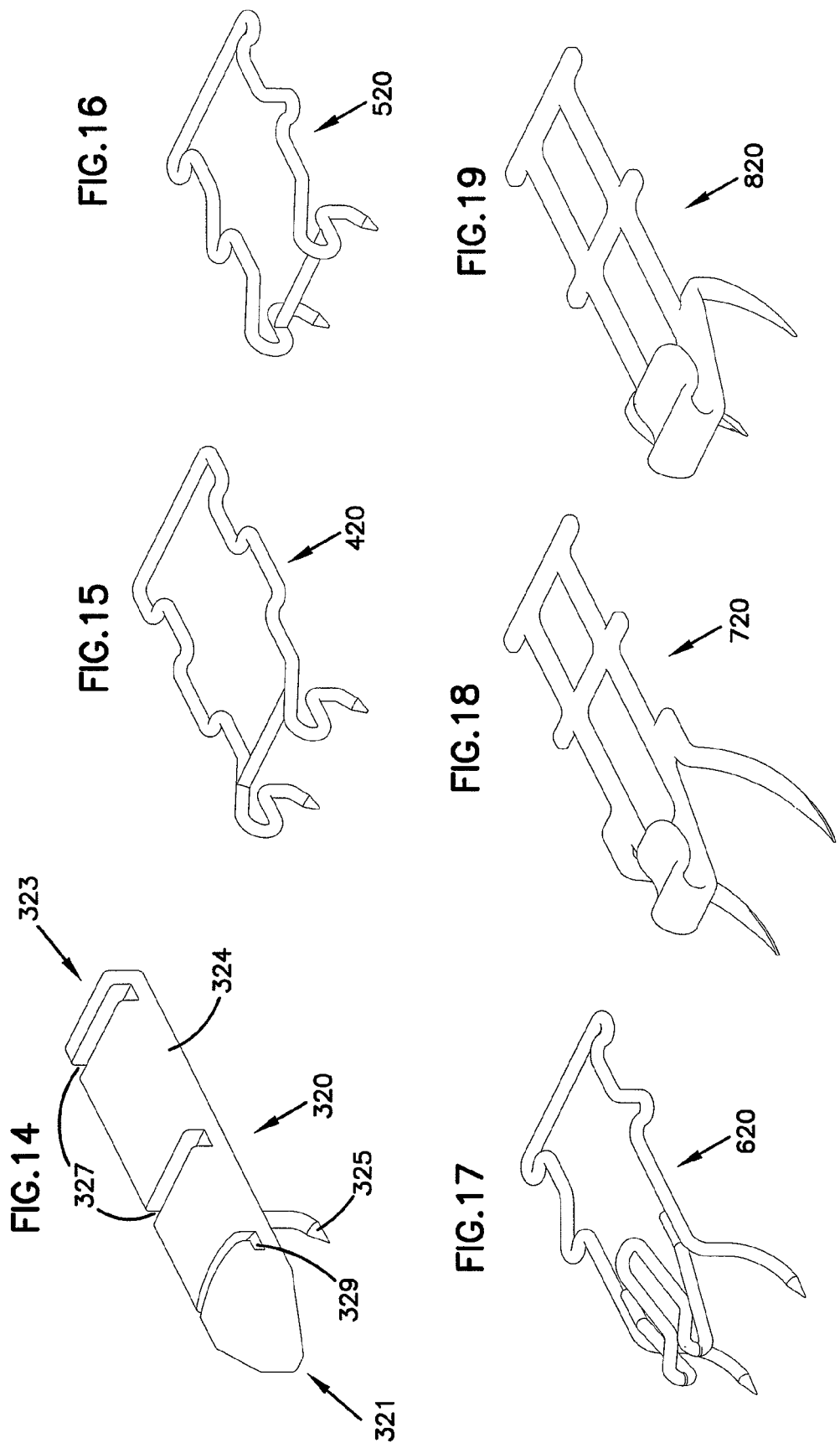

WOUND CLOSURE PRODUCT

CROSS REFERENCE TO RELATED APPLICATIONS

This application is a continuation of application Ser. No. 13/149,084, filed May 31, 2011, now U.S. Pat. No. 8,469,997, which is a continuation of application Ser. No. 12/217,513, filed Jul. 3, 2008, now U.S. Pat. No. 7,972,362, which is a continuation of application Ser. No. 10/949,115, filed Sep. 13, 2004, now U.S. Pat. No. 7,455,681, which applications are incorporated herein by reference in their entirety.

TECHNICAL FIELD

The principles disclosed herein relate generally to wound closure by facilitating stretching of skin tissue. More specifically, the disclosure relates to a system and method of facilitating expanding the skin tissue over a wound by use of dynamic force.

BACKGROUND

Surgical procedures such as tumor removal or fasciotomies can result in large skin wounds. Chronic wounds such as diabetic ulcers frequently do not heal. Techniques have been developed to facilitate the wound closure of large skin defects and chronic wounds.

Common methods for closure of wounds and skin defects include split thickness skin grafting, flap closure and gradual closure utilizing tissue expansion. A split thickness skin graft involves removing a partial layer of skin from a donor site, usually an upper leg or thigh, and leaving the dermis at the donor site to re-epithelialize. In this manner, a viable skin repair patch can be transferred or grafted to cover the wound area. The graft is often meshed, (which involves cutting the skin in a series of rows of offset longitudinal interdigitating cuts) allowing the graft to stretch to cover an area two or three times greater than the wound, as well as provide wound drainage while healing. Normal biological function of the skin heals the cuts after the graft has been accepted. A meshed graft of this type requires a smaller donor area than a conventional non-meshed or full thickness skin graft. Flap closure involves transferring skin from an adjacent region to the wound. This technique is only effective in anatomical regions that are amenable to transfer of adjacent skin. It is also a more complex surgical procedure involving increased surgical costs and risks. Both of these methods do not provide optimal cosmesis or quality of skin cover. Other disadvantages of these methods include pain at the donor site, creation of an additional disfiguring wound, and complications associated with incomplete "take" of the graft. In addition, skin grafting often requires immobilization of the limb, which increases the likelihood of contractures. The additional operation and prolongation of hospital stay is an additional economic burden.

Gradual, or progressive, closure is another method of wound closure. This technique may involve suturing vessel loops to the wound edge and drawing them together with large sutures in a fashion similar to lacing a shoe. In addition, the wound edges may be progressively approximated with suture or sterile paper tape. The advantages of this gradual, or progressive, technique are numerous: no donor site is required for harvest of a graft; limb mobility is maintained; superior cosmetic result, more durable skin coverage, better protection because skin is full thickness, and maintenance of normal skin sensation may all be achieved.

Existing devices for effecting a gradual closure, however, have many disadvantages. Current methods and devices rely on static or elastic ribbon or suture material which must be repeatedly readjusted in order to draw wound edges together because a relatively small skin movement substantially eliminates much of the closure force. Even with constant readjustment, maintenance of near constant tension over time is difficult, if not impossible, to achieve. Since widely used existing closure techniques involve use of relatively inelastic materials such as sutures or surgical tape, a substantial amount of tension is put on the wound edges during periodic adjustment to obtain the necessary closure force. Excessive tension may cut the skin or cause necrosis due to point loading of the tissue.

Other approaches use a pulling force across a linear path over the wound. This approach obscures the wound from viewing and must be removed every two or three days for adjustment and to dress the wound. Multiple devices are required to close most wounds.

What is needed in the art is a gradual wound closure technique that is self-regulating and self-adjusting and uses continuous or dynamic tension to draw the wound edges together, without obstructing the wound or needing multiple devices thus eliminating the need for constant readjustment involved with the static systems.

SUMMARY

The principles disclosed herein relate to wound closure by facilitating stretching of skin tissue. The disclosure relates to a system and method of facilitating expanding the skin tissue over a wound by use of dynamic force.

The disclosure is directed to a wound closure system including components adapted to apply a dynamic tension force on a plurality of anchors that are attached to skin tissue surrounding a wound. The dynamic tension force draws the anchors toward the wound facilitating stretching of the skin tissue over the wound area.

In one particular aspect, the disclosure is directed to a wound closure system comprising a plurality of skin anchors mechanically attached to external skin tissue around a periphery of a wound and a line extending between the skin anchors. The line extends around substantially the entire periphery of the wound and application of tension to the line draws the skin anchors toward each other and toward the wound.

In another particular aspect, the disclosure is directed to a wound closure system comprising a plurality of skin anchors mechanically attached to external skin tissue around a periphery of a wound, a line extending between the skin anchors, the line slidably engaged with each skin anchor, and a biasing member that provides tension on the line to draw all of the skin anchors toward each other and toward the wound.

In yet another particular aspect, the disclosure is directed to a method of closing a wound, the method comprising the steps of attaching a plurality of skin anchors to external skin tissue around a periphery of a wound, extending a line among the skin anchors around substantially the entire periphery of the wound, and providing tension to the line to draw the skin anchors toward each other and toward the wound.

In yet another particular aspect, the disclosure is directed to a wound closure kit comprising a plurality of skin anchors adapted for attachment to external skin tissue, a line adapted to be slidably engaged with each skin anchor, and a biasing member adapted to provide tension on the line.

In yet another particular aspect, the disclosure is directed to an alternative use of the wound closure system where the wound closure system may be used for cosmetic purposes to stretch the skin at certain parts of the body that do not include wounds.

BRIEF DESCRIPTION OF THE DRAWINGS

FIG. 7A is a top perspective view of a cover of the tensioning apparatus of FIG. 2;

FIG. 8A is a top perspective view of a skin anchor suitable for use with the wound closure system of FIG. 1;

FIG. 8B is a top plan view of the skin anchor of FIG. 8A;

FIG. 8C is a side elevation view of the skin anchor of FIG. 8A;

FIG. 8D is a front view of the skin anchor of FIG. 8A;

FIG. 10B is a bottom perspective view of the cover of FIG. 10A;

FIG. 14 is a top perspective view of a fourth embodiment of a skin anchor suitable for use with the wound closure system of FIG. 1;

FIG. 15 is a top perspective view of a fifth embodiment of a skin anchor suitable for use with the wound closure system of FIG. 1;

FIG. 16 is a top perspective view of a sixth embodiment of a skin anchor suitable for use with the wound closure system of FIG. 1;

FIG. 17 is a top perspective view of a seventh embodiment of a skin anchor suitable for use with the wound closure system of FIG. 1;

FIG. 18 is a top perspective view of an eighth embodiment of a skin anchor suitable for use with the wound closure system of FIG. 1;

FIG. 19 is a top perspective view of a ninth embodiment of a skin anchor suitable for use with the wound closure system of FIG. 1;

DETAILED DESCRIPTION

The inventive aspects of the disclosure will now be described by reference to the several drawing figures. The functional features of the inventive aspects can be embodied in any number of specific configurations. It will be appreciated, however, that the illustrated embodiments are provided for descriptive purposes and should not be used to limit the inventions described herein.

A. Wound Closure System

Figure 1:
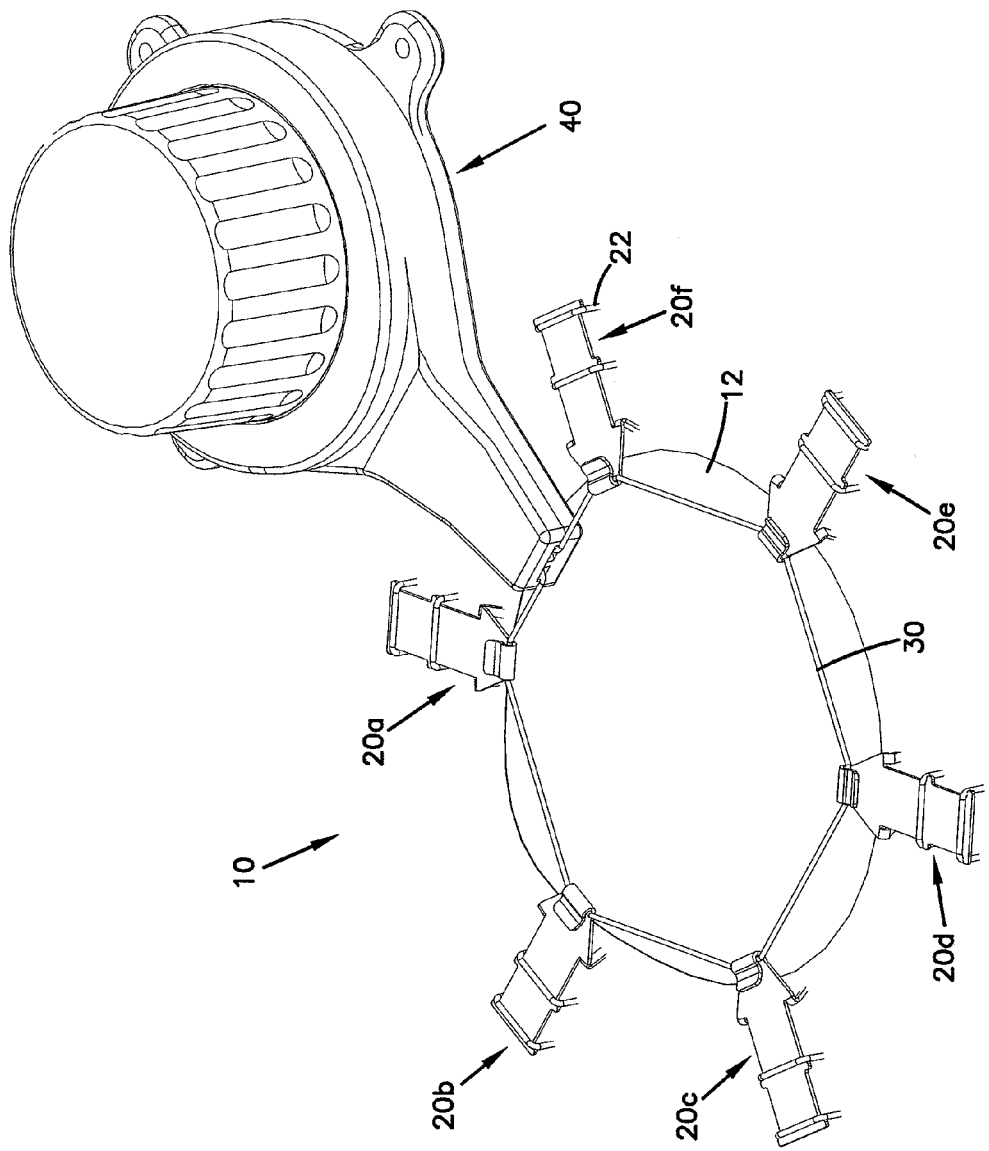
FIG. 1 is a perspective view of a wound closure system in accordance with the principles of the present disclosure.

FIG. 1 illustrates one embodiment of a wound closure system 10 having features that are examples of inventive aspects disclosed herein. The wound closure system 10 includes a plurality of anchors 20 (individually indicated as 20a, 20b, 20c, 20d, 20e, and 20f) positioned around the periphery of a wound 12. Anchors 20a, 20b, 20c, etc. are attached to the skin surrounding wound 12 by mechanical means (e.g., staples). Anchors 20a, 20b, 20c, etc. are connected to one another by a tension line 30. Line 30 is movably attached to each anchor 20; typically line 30 is slidably attached to anchors 20 so that it can slide relative to each of the anchors. Although line 30 is illustrated in FIG. 1 as being attached to anchors 20a, 20b, 20c, etc. so that it extends around substantially the entire periphery of wound 12, line 30 can also be attached to anchors 20a, 20b, 20c, etc. in a manner as to extend across the wound 12, i.e., in a "shoe-lace" configuration, although not preferably. Preferably, however, the tension line 30 is looped to extend around the periphery of the wound, which leaves the wound accessible for inspections and dressing changes.

The wound closure system 10 may also include a tensioning apparatus 40 that is adapted to apply tension to line 30 to draw the anchors 20, and thus the skin, inwardly toward each other and thus over the wound 12. Although depicted as including a separate tensioning apparatus in FIG. 1, the wound closure system may instead utilize a line 30 that includes elastic material to provide the dynamic tension on the skin anchors 20. With the use of a tension apparatus 40, however, an inelastic line 30 can be utilized to draw the skin anchors 20 toward the wound 12 since the tensioning apparatus is adapted to provide the dynamic force needed for wound closure. An elastic line 30 can also be used in addition to a separate tensioning apparatus 40.

In a preferred embodiment, tensioning apparatus 40 includes a biasing member 50 (shown in FIGS. 2 and 5) mounted within the tensioning apparatus 40 to provide the dynamic tension force on the skin anchors 20. As the skin stretches and grows over the wound 12, anchors 20a, 20b, 20c, etc. move toward each other and toward the wound 12, reducing the tension on line 30 and creating "slack" on the tension line 30. Biasing member 50 provides tension to take up the slack on the line 30. Although depicted as a coiled spring in FIGS. 2 and 5, the biasing member 50 may include other structures. The biasing member 50 may include a constant-force spring designed to provide a constant level of tension on the line 30 when it is in a loaded state. The biasing member 50 may alternatively include a nonconstant-force spring designed to provide varying amounts of force on the line 30 depending upon how tightly it is wound. As one skilled in the art will appreciate, the force application characteristics of such springs depend upon factors such as the mechanical properties of the springs.

In certain embodiments, the tension force that is applied to each skin anchor is usually at least 1 oz. and usually no greater than 64 oz., commonly between 4 and 16 oz.

The tensioning apparatus 40 of the wound closure system 10 can be secured to a patient by surface attachment such as by adhesives, by suturing, or by other methods as will be discussed in further detail below. The tensioning apparatus 40 can also be located at an alternate location remote from the patient's body, but preferably is proximate to the wound area.

The wound closure system 10 can be used to close a wound up to about 10 cm in diameter, although it is recognized that this will vary, depending on circumstances.

B. Tensioning Apparatus

Figure 2:
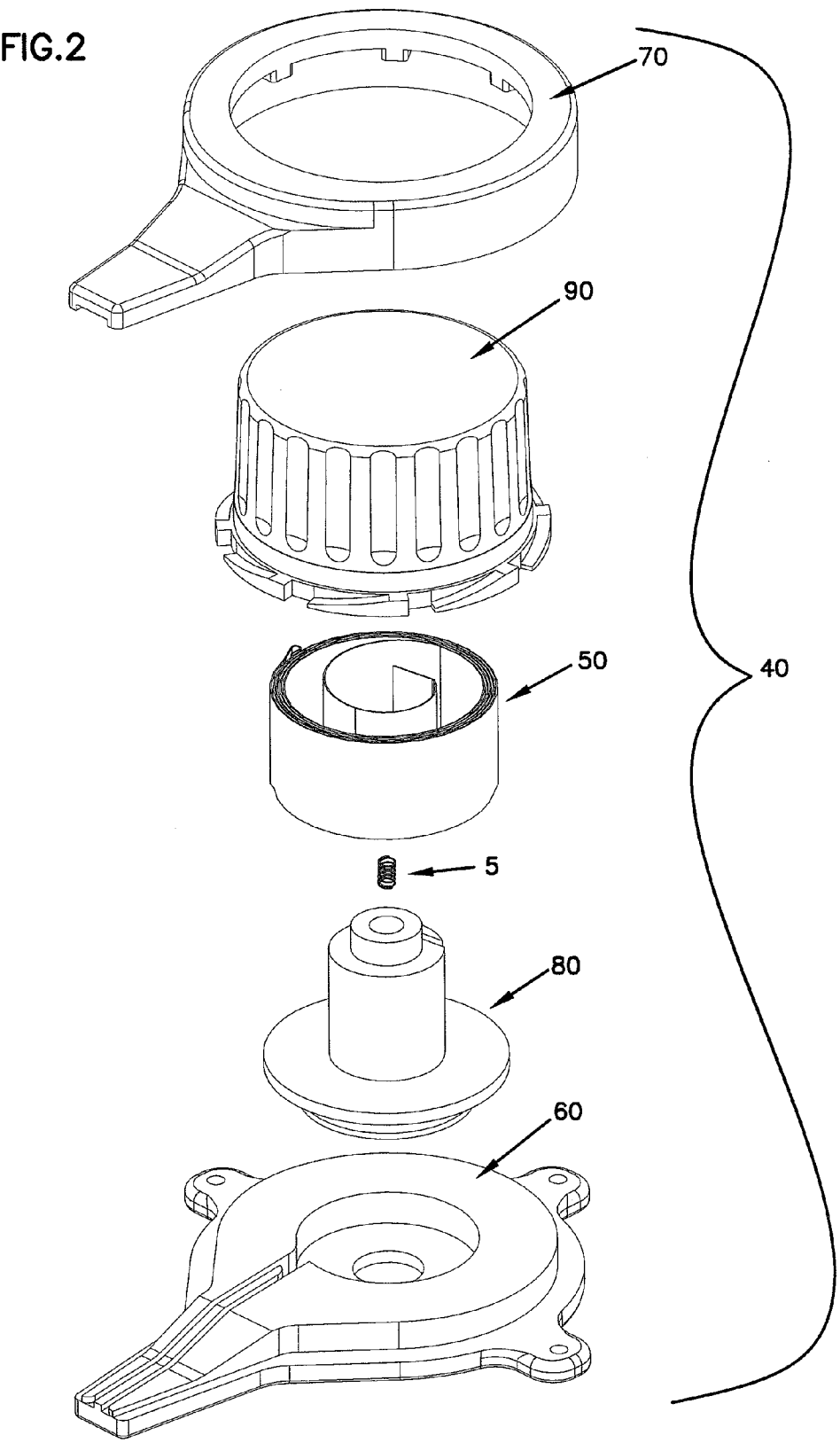
FIG. 2 is an exploded perspective view of a tensioning apparatus of the wound closure system of FIG. 1.

Referring to FIG. 2, an exploded perspective view of the tensioning apparatus 40 of the wound closure system 10 is illustrated therein. The tensioning apparatus 40 includes a base 60, a cover 70, a spool 80 that seats on the base 60, the biasing member 50 that is placed around the spool, a linear spring 5 that is inserted into the spool, and a knob 90 used to wind the biasing member 50 for application of tension.

Figure 3A:
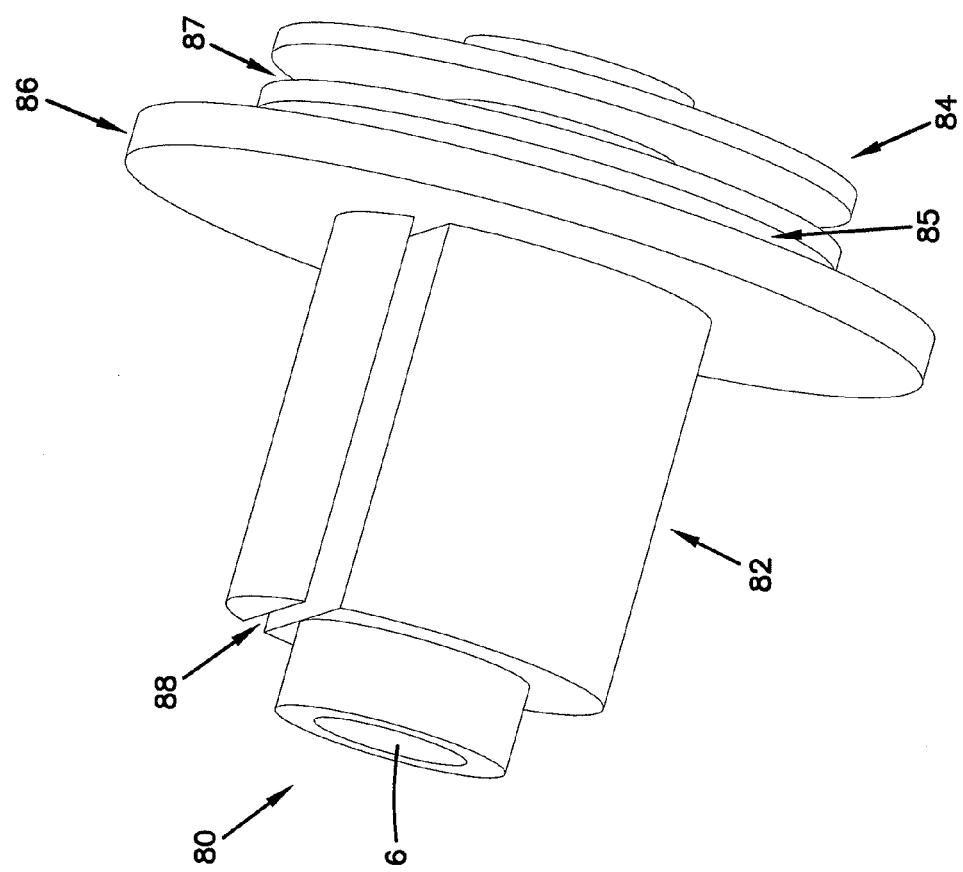
FIG. 3A is a top perspective view of a spool of the tensioning apparatus of FIG. 2.
Figure 3B:
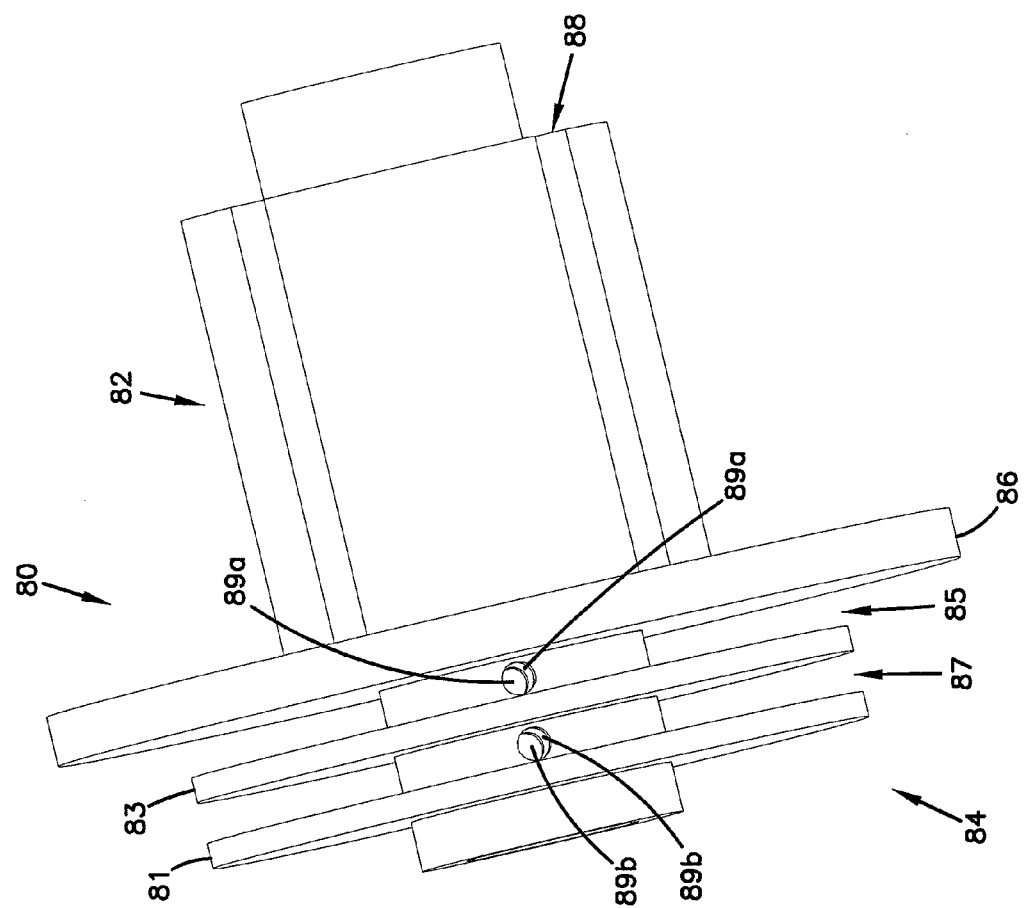
FIG. 3B is a side elevation view of the spool of FIG. 3A.
Figure 3C:
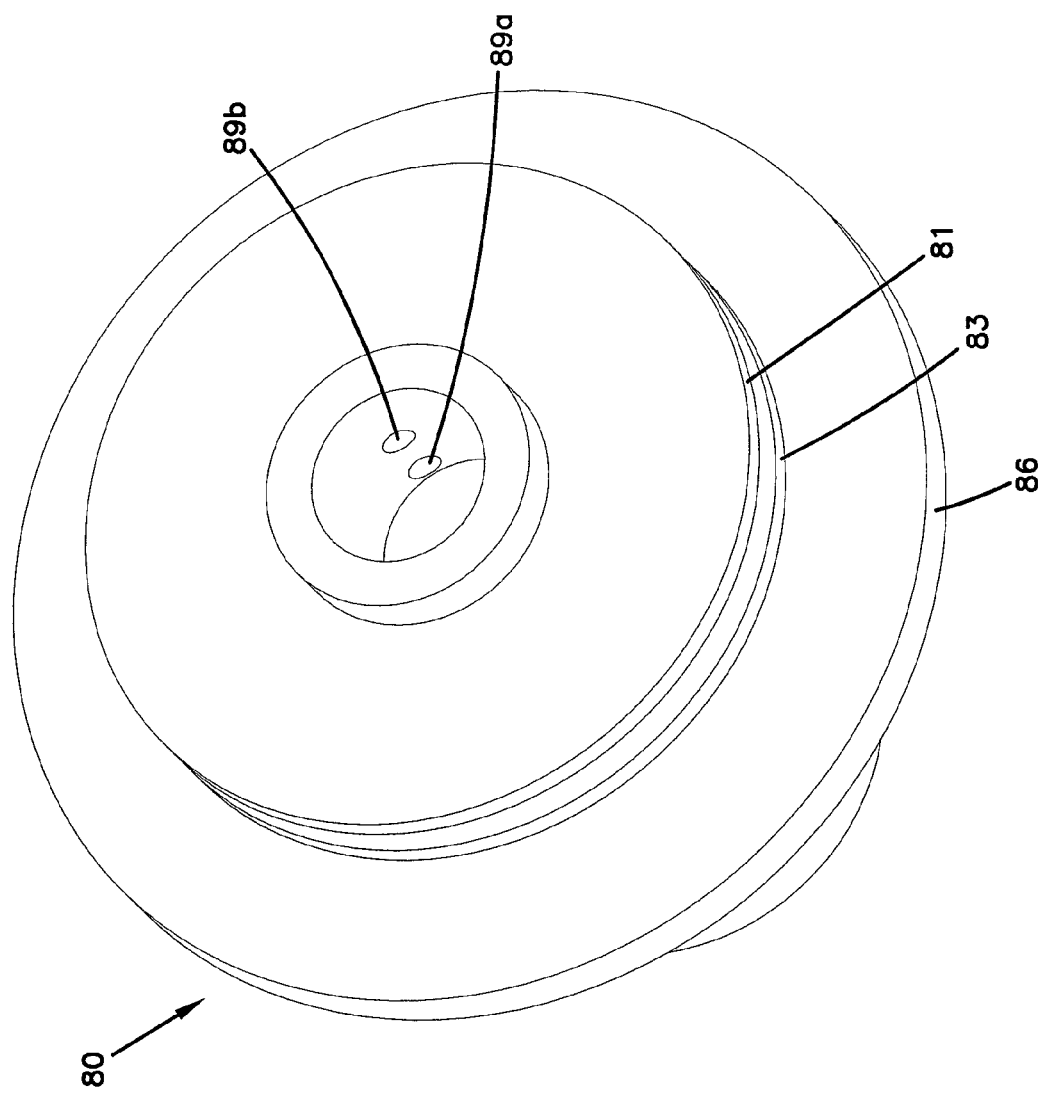
FIG. 3C is a bottom perspective view of the spool of FIG. 3A.

Referring to FIGS. 3A-3C, there is generally illustrated the spool 80 of the tensioning apparatus 40. The spool 80 includes an upper spring mount portion 82, a lower tension line mount portion 84, and a main plate 86 separating the two portions. In this embodiment, all the portions of the spool 80 are depicted as integrally formed from one unitary piece. However, it will be appreciated that in other embodiments, the spool may be formed from multiple separate pieces that are coupled together.

The upper spring mount portion 82 has a generally cylindrical shape. The upper mount portion 82 includes a slot 88 adapted to receive one end of the biasing member 50 as will be discussed in further detail below. The upper spring mount portion 82 also includes a well 6 for the placement of the linear spring 5 (seen in FIG. 2), the purpose of which will be discussed in further detail below. The well 6 is not a throughhole and extends only about halfway down the length of the upper spring mount portion 82. The linear spring 5 is sized such that when the linear spring 5 is placed within the well, a portion of the spring 5 protrudes upwardly out of the well (not shown in the FIGS.).

The lower tension line mount portion 84 defines two winding grooves 85, 87. The lower winding groove 87 is defined between two seat plates, a lower seat plate 81 and an upper seat plate 83. The upper winding groove 85 is defined between the main plate 86 and the upper seat plate 83. The seat plates 81, 83 provide structure for seating the spool 80 into the base 60 of the tensioning apparatus. The spool 80 also defines a pair of holes 89, an upper hole 89a and a lower hole 89b, located on two opposing sides of the spool 80, as best seen in FIG. 3B. Only one pair of the holes 89 is seen in FIG. 3C. The upper holes 89a are defined within the upper winding groove 85 between the main plate 86 and the upper seat plate 83 and the lower holes 89b are defined within the lower winding groove 87 between the two seat plates 81 and 83. The holes 89a and 89b are used to couple a length of line 30 to the spool 80.

For example, to couple the line 30 to the spool, a first end of the line 30 is threaded through hole 89a. A knot is tied, the knot being large enough that the first end of the line 30 will not slip through the hole. The other end of the line 30 is threaded through hole 89b located in the lower winding groove 87 and a similar knot is tied. In this manner, the line 30 can be coupled to the spool ready to be wound. The two ends of the line 30 are preferably attached to holes in separate winding grooves to facilitate winding of the line 30 and keep line 30 untangled during winding. The ends of the line may be coupled on opposing sides of the spool or they may be coupled on the same side of the spool as long as they are kept in separate winding grooves to reduce any kind of tangling of the line 30.

Figure 4:
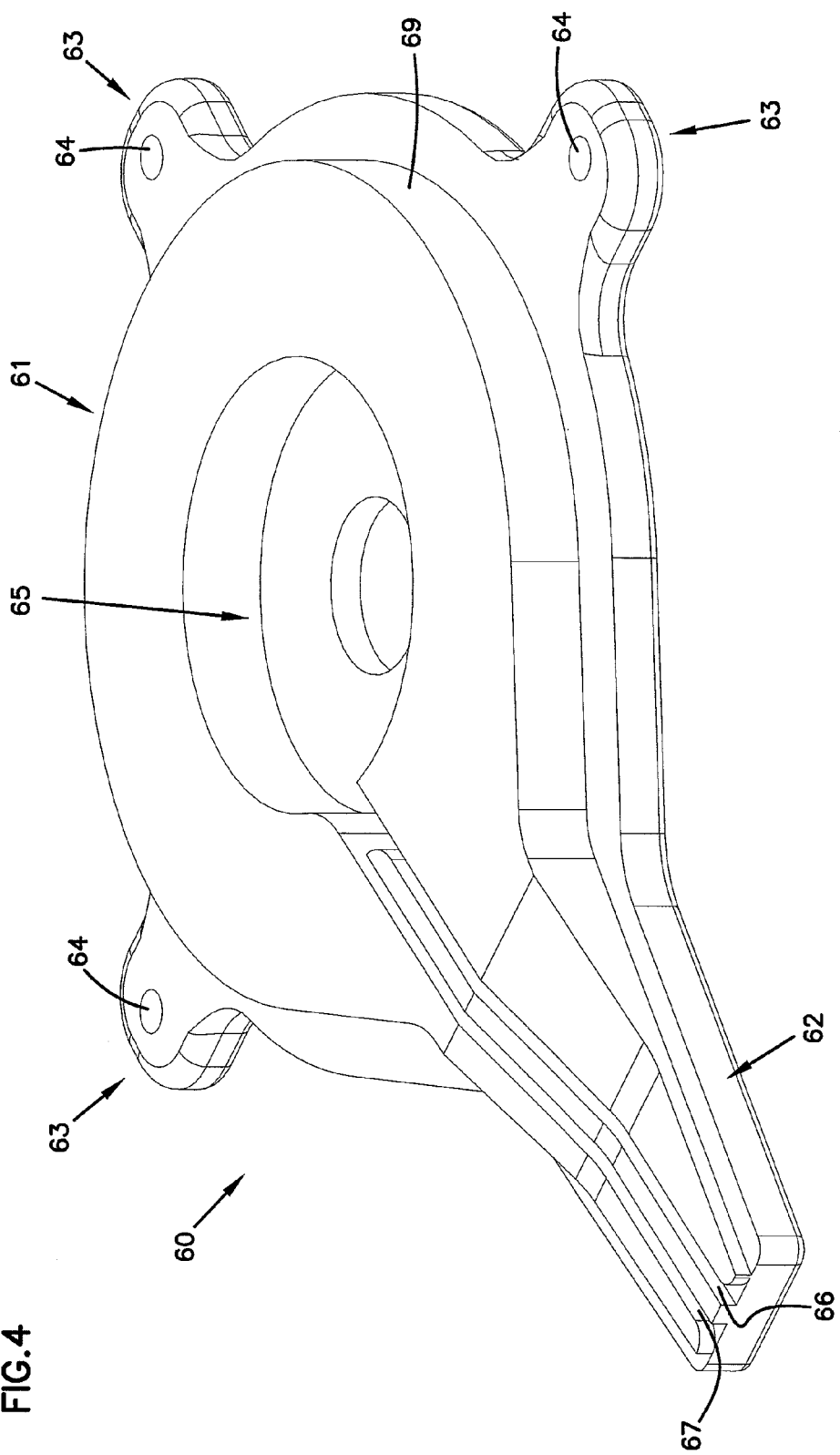
FIG. 4 is a top perspective view of a base of the tensioning apparatus of FIG. 2.

Referring to FIG. 4, there is generally illustrated the base 60 of the tensioning apparatus 40. Base 60 includes a generally circular main body portion 61 and an elongated snout portion 62. Disposed around the main body 61 are three legs, generally indicated at 63 that may be used to mount the base 60 to exterior skin tissue. Each leg 63 is depicted as including a suture hole 64 for suturing the base 60 to skin. Although depicted as being adapted for mounting to the skin by way of suturing, the base need not have the suture holes 64 and can be mounted to skin in other ways such as by adhesives, straps, etc. As discussed previously, the base 60 and hence the entire tensioning apparatus 40 can also be located at a location outside the patients body if desired, preferably proximate to the wound area 12.

The base 60 defines an upper mounting portion 69 protruding upwardly from the base. The mounting portion 69 defines an interior cavity 65 shaped to receive the lower tension line mount portion 84 of the spool 80. The mounting portion 69 of the base 60 also defines two elongate parallel slots 66, 67 running from the front of the snout portion 62 to the inner cavity 65. The slots 66, 67 are used to seat the tension line 30 extending from the spool 80 to the periphery of the wound 12, as will be discussed in further detail below. Preferably, slots 66 and 67 seat the two portions of the line 30 coming from different winding grooves of the spool. In this manner, the two portions of the line 30 are kept entirely separated by the slots 66 and 67, although uniform tension is provided on both ends of the line by the spool 80. By keeping the two ends of the line 30 separate with the two slots 66 and 67, the line 30 can also be unwound in an easier manner during initial set-up and readjustment phases, without the possibility of the line getting tangled. It is possible, though not preferable, to have a single slot, or even no definite structure for maintaining line 30.

The snout portion 62 of the base is provided with an elongate shape so that the portions of the tension line 30 coming out of the base 60 can be in line with the skin anchors 20 located around the periphery of the wound 12, as seen in FIG. 1. In this manner, an even distribution of pulling force can be kept on the skin around wound 12 since the tension line 30 keeps a shape corresponding to the periphery of the wound, which is generally a circular shape. Depending on the shape of the wound, the snout portion 62 of the base 60 can be placed at various positions depending on where the force is desired to be concentrated. By providing structural support for the line 30, the snout portion 62 can also allow the tensioning apparatus 40 to be positioned at a remote location from the wound 12. Remote placement of the tensioning apparatus 40 makes it easier to inspect and dress the wound 12.

Figure 5:
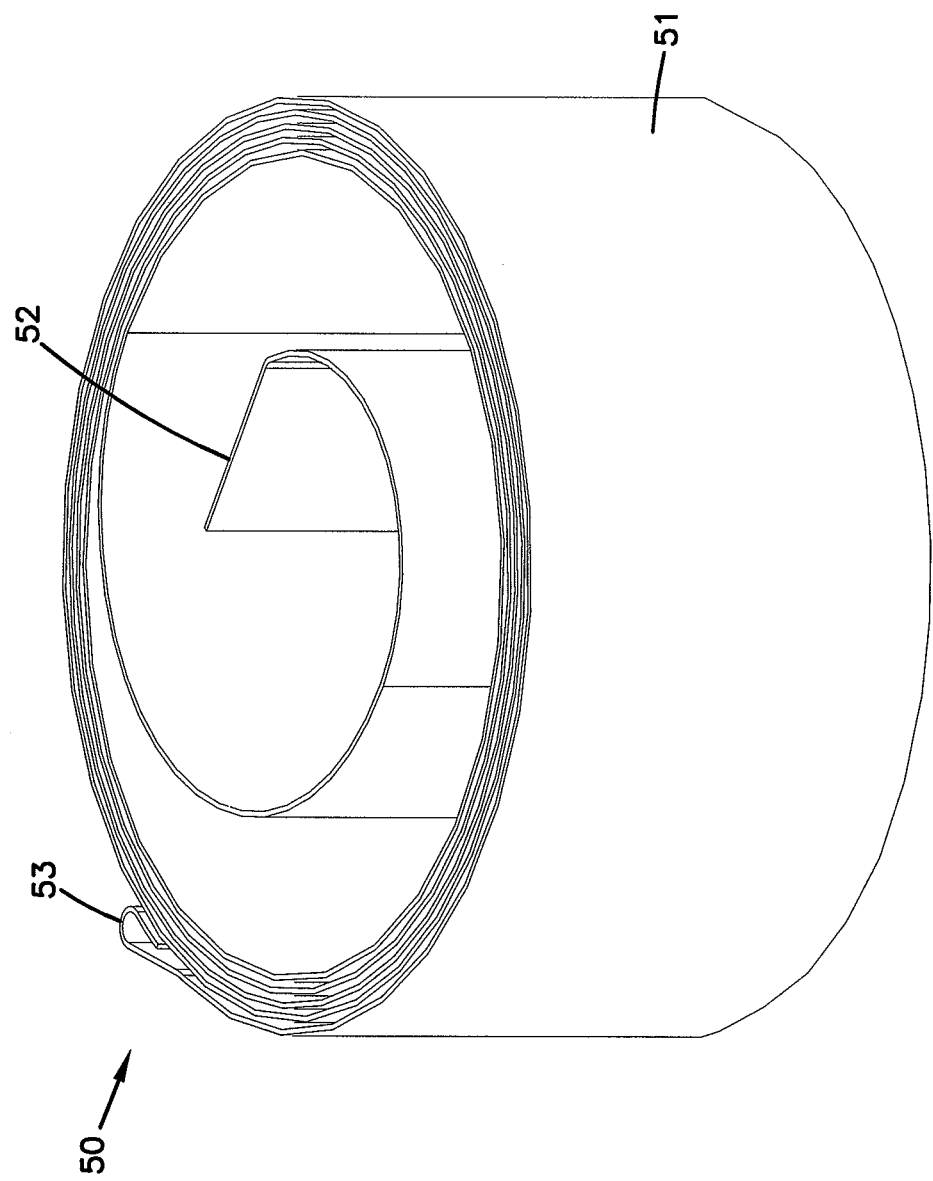
FIG. 5 is a top perspective view of a biasing member of the tensioning apparatus of FIG. 2.

Referring to FIG. 5, there is generally illustrated therein the biasing member 50 of the tensioning apparatus 40. The biasing member 50 is depicted as a spring essentially formed from a coiled-up metal band 51. As discussed previously, the spring can be a constant force spring that provides a constant level of tension regardless of how tight it is wound or it can be a nonconstant-force spring that provides different levels of tension at different degrees of tightening. In a preferred embodiment, the band 51 is made of type 301 high-yield stainless steel. In certain embodiments, the biasing member 50 can provide a load force of about 4 lbs. As will be appreciated in the art, the load force of the biasing member 50 can vary depending on certain properties such as the thickness, the diameter, or the material of the band 51.

The band 51 defines an inner end 52 and an outer tab portion 53. The coiled up band 51 is positioned around the upper spring mount portion 82 of the spool 80. When positioned as such, the inner end 52 of the band 50 is placed within the slot 88 defined on the upper spring mount 82 of the spool 80. The outer tab 53 of the band 51 cooperates with the knob 90 of the tensioning apparatus 40 for winding purposes. Winding of the biasing member 50 will be described in detail further below.

Figure 6A:
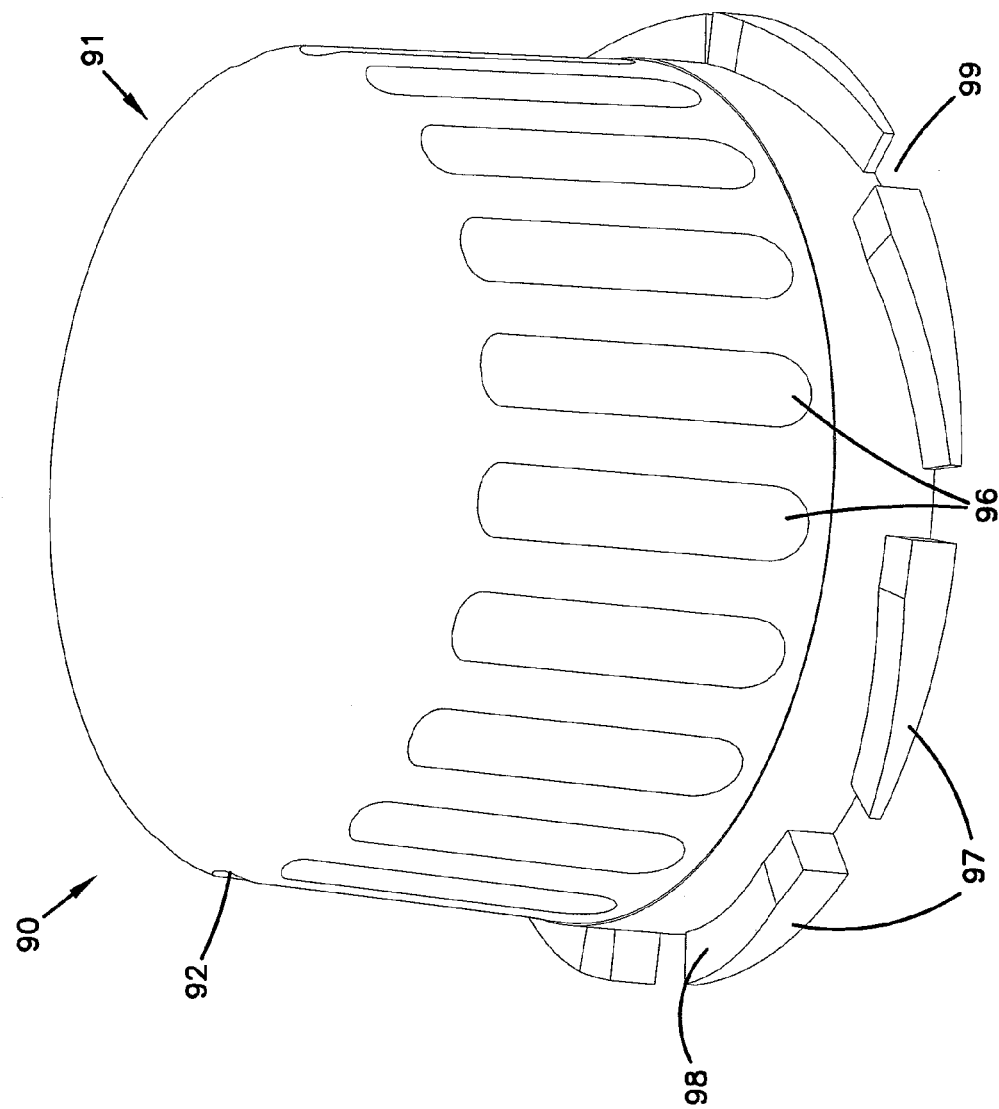
FIG. 6A is a top perspective view of a knob of the tensioning apparatus of FIG. 2.
Figure 6B:
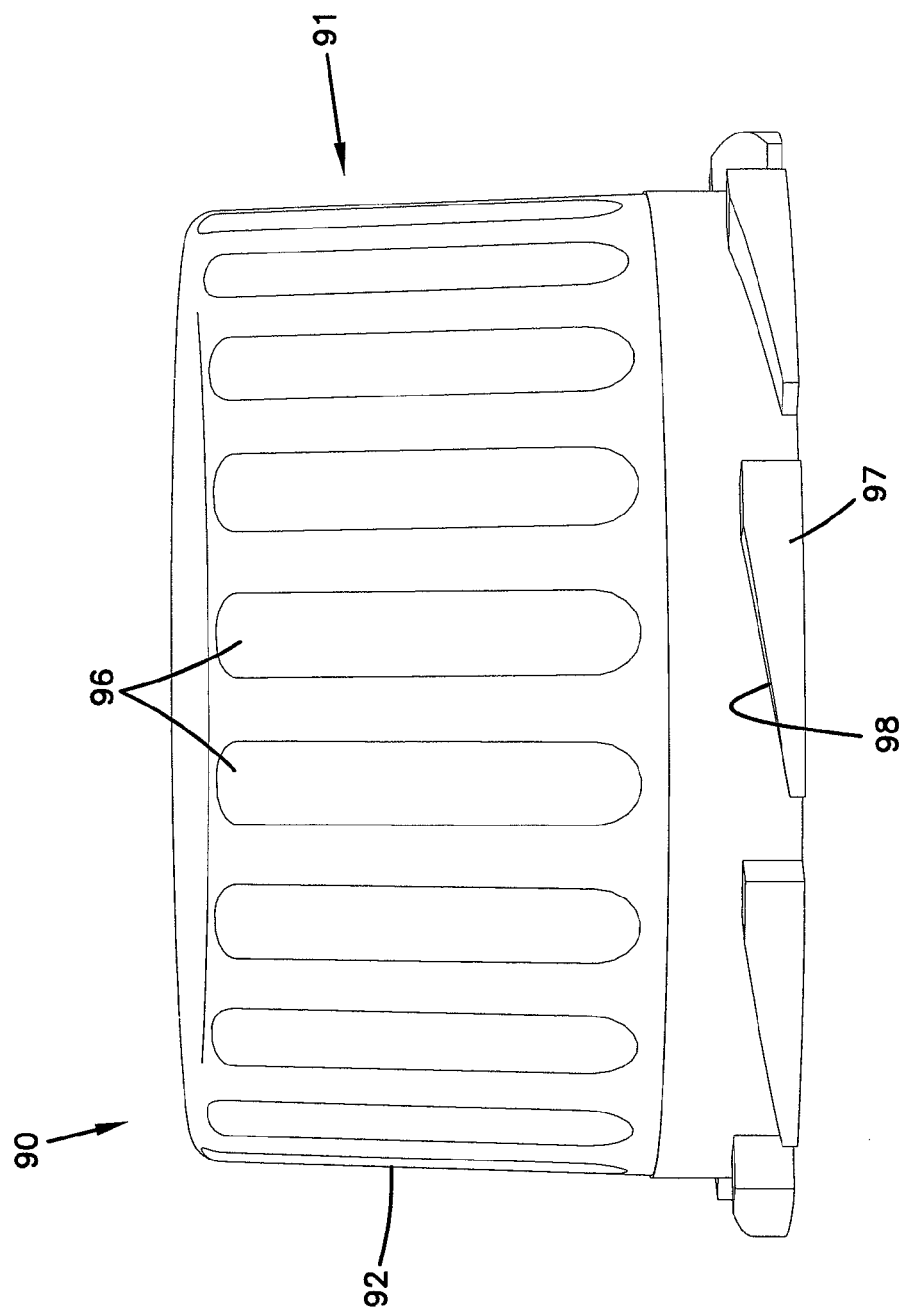
FIG. 6B is a side elevation view of the knob of FIG. 6A.
Figure 6C:
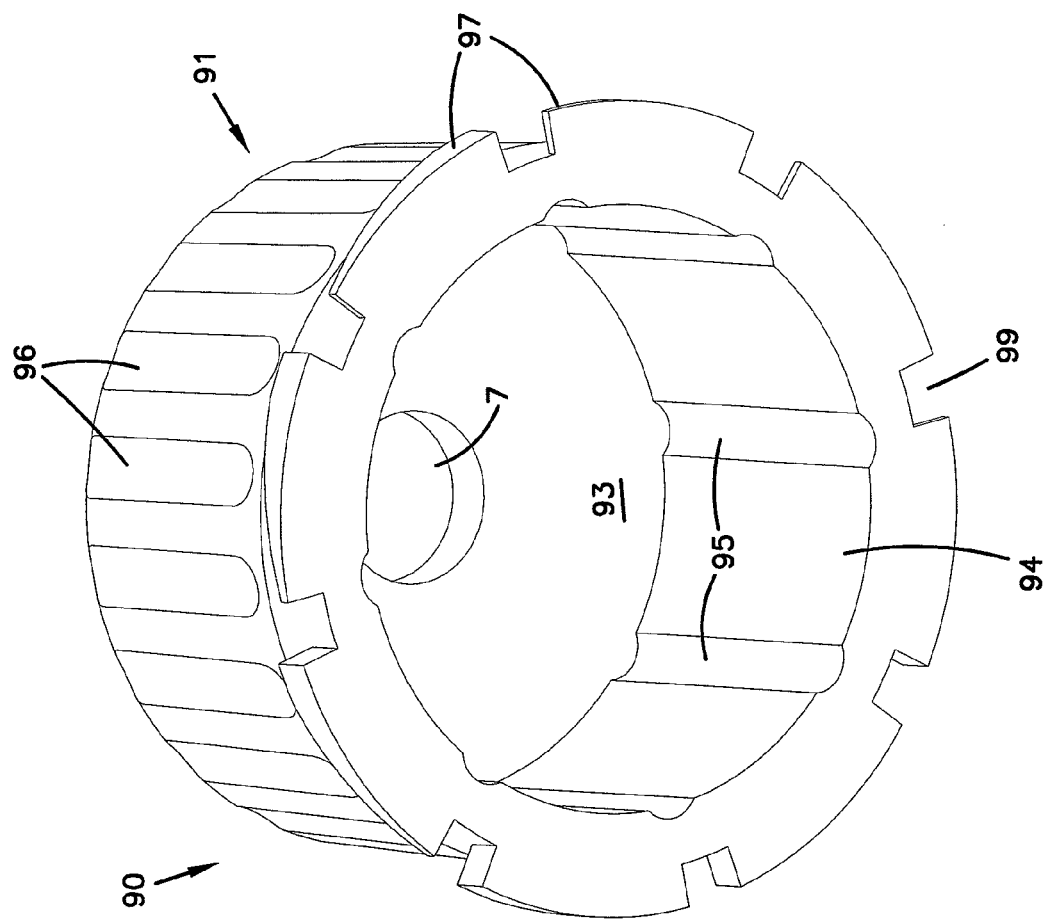
FIG. 6C is a bottom perspective view of the knob of FIG. 6A.

Referring to FIGS. 6A-6C, there is generally illustrated the knob 90 of the tensioning apparatus 40 that is used to load and unload the biasing member 50. The knob 90 includes a generally cylindrical body 91 with an exterior surface 92 and an interior cavity 93 defined by an interior surface 94. The interior cavity 93 is shaped and sized to tightly receive the biasing member 50. The interior surface 94 includes radially arranged vertical indents 95 that cooperate with the outer tab 53 of the biasing member 50 to wind the biasing member, as will be discussed in further detail below. The interior surface also includes a slot 7 adapted to receive a portion of the linear spring 5 (seen in FIG. 2) that protrudes out of the upper spring mount portion 82 of the spool 80.

The exterior surface 92 of the knob 90 defines radially arranged gripping features 96 to facilitate turning the knob during winding. The gripping features 96 are depicted as vertical grooves but may be other structures adapted to facilitate the winding process of the biasing member 50.

The exterior surface 92 of the knob 90 also includes horizontal tabs 97 arranged radially around the circumference of the knob. The tabs 97 include ramped surfaces 98 that ramp upwardly to a land area in a counterclockwise direction. The tabs 97 are spaced and define rectangular gaps 99 therebetween. The tabs 97 cooperate with the cover 70 of the tensioning apparatus 40 to wind the biasing member 50, to lock the biasing member 50 when it is loaded, and to release the biasing member 50 when desired, as will be described below in further detail.

Figure 7B:
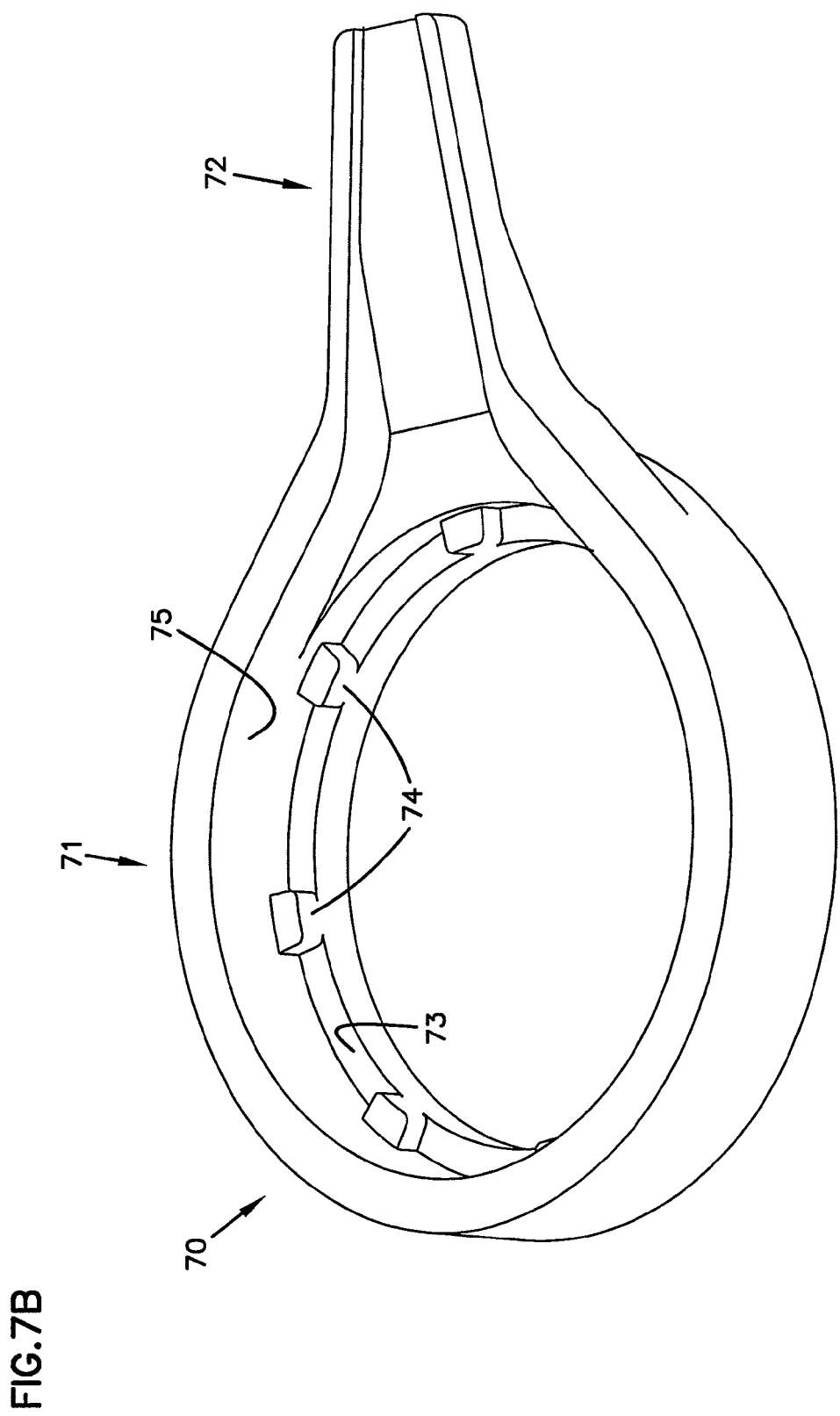
FIG. 7B is a bottom perspective view of the cover of FIG. 7A.

Referring to FIGS. 7A-7B, there is generally illustrated therein the cover 70 of the tensioning apparatus 40. The cover 70 generally includes an interior shape configured to fit on exterior of the base 60. The cover includes a main body portion 71 and an elongate snout portion 72. The main body portion 71 fits over the main body portion 61 of the base 60 and the snout portion 72 fits over the snout portion 62 of the base 60. The cover 70 includes an inner wall 75 that is shaped and sized to snugly fit over the mounting portion 69 of the base 60.

As seen in the bottom perspective view of the cover 70 in FIG. 7B, the inner wall 75 of the cover 70 defines a flange 73 surrounding the inner perimeter of the main body portion 71. The flange 73 is adapted to trap the horizontal side tabs 97 of the knob 90 to capture the knob 90 in between the base 60 and the cover 70 of the tensioning apparatus 40. The flange 73 defines radially arranged rectangular tabs 74 that are adapted to slide over the ramped surfaces 98 of the horizontal tabs 97 of the knob 90 and fit into the rectangular gaps 99 defined between the horizontal tabs 97 as the knob is turned clockwise, as will be described in further detail below. The cover 70 may be coupled to the base 60 by various methods including friction fit, by adhesives, by fasteners, by a snap fit, etc.

The tensioning apparatus 40 can either be located near the wound area 12 or away from the wound area 12. In certain embodiments, the tensioning apparatus can be secured to the patient by methods such as by suturing, by adhesive, adhesive tape, a bandage, or wound dressing. In other embodiments, the tensioning apparatus can be located away from a patient's body.

C. Skin Anchors

As seen in FIG. 1, a plurality of anchors 20a, 20b, 20c, etc. are placed around the periphery of the wound 12. Each anchor 20 is mechanically fastened to the skin, such as by conventional medical skin staples 22. Suturing can also be used to mechanically attach the anchors 20 to the skin.

Referring to FIGS. 8A-8D, the anchor 20 includes a first end 21, a second opposite end 23, and a generally rectangular body 24 defined between the first end 21 and the second end 23. The anchor 20 includes two skin-penetrating barbs 25 proximate the first end 21 for securement to the skin. The barbs 25 preferably have a bearing surface with a large enough width perpendicular to the direction of the tension so that the barbs 25 do not cut through the skin when pulled toward the wound in tension. In this manner, as the barbs 25 move in toward the wound, the skin moves with the barbs. The barbs 25 can be bent at an angle $A_B$ less than about 90 degrees from the skin surface. The barbs 25 can be bent, preferably, at about a 60 degree angle $A_B$ to improve their ability to hold into the skin. The edges of the barbs 25 are sharp to make it easy to penetrate the skin upon insertion. Two pairs of indentations, generally indicated at 26 are formed on the body 24 of the anchors to help guide where mechanical attachment, such as staples 22, are to be placed. Two pairs of tabs 27 extending out from the opposing sides of the body 24 are adapted to abut against the staples 22 to pull the skin toward the wound 12. Although the guiding indentations 26 are located forward of the tabs 27, as the anchors 20 are pulled in toward the wound 12, the tabs 27 eventually abut against the staples 22 after initial stretching of the skin around the wound area is achieved.

A tension line tab 28 defines a tension line slot 29 formed at the first end 21 of the anchor 20 for receiving the tension line 30. The tension line slot 29 is formed with a wide lead-in area to make it easy to receive the tension line 30. The tension line slot 29 is sized such that the tension line 30 is "snapped-in" past the narrowest point of the slot 29 to prevent the line from accidentally being pulled out.

Anchor 20 includes a length $L_A$. The barbs 25 include a penetration depth $D_P$. The inner edges of the barbs 25 are spaced apart a distance of $W_B$. The dimensions, $L_A$, $D_P$, $W_B$, and $A_B$ can be varied according to desired skin anchor performance in different parts of the human body and for different types and ages of skin.

Table 1, below, illustrates two example configurations for the anchor, with two different sets of dimensions that are suitable for use with the wound closure system 10. Anchors with example configuration 1 are preferably retained by two conventional regular size medical skin staples (5.7 mm×3.9 mm). Anchors with example configuration 2 are preferably retained by two wide size medical skin staples (6.9 mm×3.9 mm).

TABLE 1

Anchors (unless otherwise specified, all dimensions are in inches)

|  | $L_A$ | $D_P$ | $W_B$ | $A_B$ |
|---|---|---|---|---|
| Configuration 1 | 0.739 | 0.158 | 0.186 | 60° |
| Configuration 2 | 0.607 | 0.115 | 0.206 | 60° |

In a preferred embodiment, the anchor 20 is formed from stainless steel sheet such as 302 or 316 containing 8 to 14% nickel content. It will be appreciated that the anchors can be stamped with a progressive die, wire EDM-cut, shaped from metal, shaped from wire, injection molded, or made by other suitable methods. The anchors can also be manufactured from other metals such as titanium.

D. Tension Line

Referring to FIG. 1, the tension line 30 of the wound closure system 10 is illustrated as being coupled to the anchors 20 around the periphery of the wound 12. The tension line 30 may be a nylon or polypropylene line, suture material, string, a cable, a wire, or other similar item. Line 30 should be sufficiently flexible and bendable to allow slidable attachment to anchors 20. In a preferred embodiment, the tension line 30 is conventional suture material. One preferred line 30 is made from nylon and has a tensile strength of about 6 lbs to 10 lbs. The tension line 30 preferably includes a thread diameter of about 0.5 mm to 0.6 mm.

Although depicted as including a separate tensioning apparatus in FIG. 1, the wound closure system 10 may instead utilize a line 30 that includes elastic material to provide the dynamic tension on the skin anchors 20. With the use of a tension apparatus 40, however, an inelastic line 30 can be utilized to draw the skin anchors 20 toward the wound 12 since the tensioning apparatus is adapted to provide the dynamic force needed for wound closure. An elastic line 30 can also be used in addition to a separate tensioning apparatus 40.

E. General Use of Wound Closure System

In general use, first, the skin anchors 20 are placed at generally equal intervals around the periphery of the wound 12. The skin engagement barbs 25 of the skin anchors 20 are then pressed into the skin. Each skin anchor 20 may then be coupled to the skin with the use of, for example, staples 22. The two pairs of indentations 26 defined on the body 24 of the skin anchors 20 serve as target areas for placement of the staples 22.

After the line 30 has been attached to the spool 80 through the holes 89a and 89b and wound around the upper and lower winding grooves 85, 87, the tensioning mechanism is assembled with the spool 80 fitting into the base 60. After winding of the line 30, the loop of line 30 is guided out of the snout portion 62 of the base 60 with the two sides of the line 30 being seated into the parallel slots 66, 67 of the base. The biasing member 50 is placed on top of the spool 80, the knob 90 is placed on top of the biasing member 50 after the linear spring 5 is placed within the well 6 of the spool 80, and the cover 70 is mounted on top of the base 60 trapping the knob 90 thereinbetween the base 60 and the cover 70.

After assembly, the loop of line 30 from the tensioning apparatus 40 is pulled out until there is enough line to fit over the tension line tabs 28 of the skin anchors 20. After line 30 is placed over all the skin anchors 20, the knob 90 of the tensioning apparatus 40 is turned clockwise. The turning of the knob 90 pulls the line 30 in and starts to wind the biasing member 50 located therewithin.

Rotating the knob 90 clockwise causes the rectangular tabs 74 on the inside of the cover 70 to ride up and over the ramped surfaces 98 of the horizontal tabs 97 of the knob 90. The linear spring 5 protruding out of the spool 80 is used to exert an upward force on the knob 90 to keep the horizontal tabs 97 of the knob 90 pressed against the flange 73 of the cover 70. A clicking sound may be heard as the rectangular tabs 74 are seated into the rectangular gaps 99 as they ride up and over the ramped surfaces 98. The interlocking of the rectangular tabs 74 within the rectangular gaps 99 prevents the knob 90 from turning backwards in a counterclockwise direction.

When the knob 90 is turned clockwise, the biasing member 50 is loaded because the outer tab portion 53 of the coiled band 51 fits into one of the vertical indents 95 causing the biasing member 50 to turn with the knob 90. When the coiled band 51 is initially in an unwound orientation, the large diameter of the band 51 creates a tight fit with the interior of the knob 90 creating a substantial amount of friction with the interior of the knob 90. In this manner, the outer tab portion 53 is kept pressed against the inner surface 94 of the knob 90, within one of the vertical indents 95. As the biasing member 50 is wound, it becomes smaller and eventually obtains a diameter small enough that the outer tab 53 no longer exerts enough friction force against the interior surface 94 of the knob 90. At this point, further winding of the knob 90 causes the outer tab portion 53 to slip out of the vertical indents 95. This slipping gives an indication that the biasing member 50 is fully wound.

Since the spool 80 is connected to the biasing member 50, turning of the knob 90 also causes turning of the spool 80, tightening the line 30 around the anchors 20. The biasing member 50 is wound to such extent that it applies a dynamic force on the line 30 pulling the skin anchors 20 in toward the wound 12. The design of the snout 62 of the base 60 makes it possible to concentrate all the pulling force into one area. The snout 62 also inhibits any pulling on the tensioning apparatus 40 because the tip of the snout 62 aligns the tensioning apparatus 40 with the loop of line 30 around the periphery of the wound 12 diverting all the tension forces to a transverse direction along the loop instead of in the direction of the snout 62 itself. As the anchors 20 move in toward the wound 12 by the stretching of the skin, the wound-up biasing member and hence the spool 80 keeps the line 30 taut.

Occasionally it may be necessary to release the line 30 to reposition it for adjustments or to remove the tensioning apparatus 40. Pushing down on the knob 90 causes the linear spring 5 (see FIG. 2) to compress and the rectangular tabs 74 on the inside of the cover 70 to disengage from the rectangular gaps 99 defined around the knob 90. This causes the knob 90 to be able to be turned backwards in the counterclockwise direction and the line 30 to come out.

F. Alternative Embodiments

1) Base of Tensioning Apparatus

Figure 9:
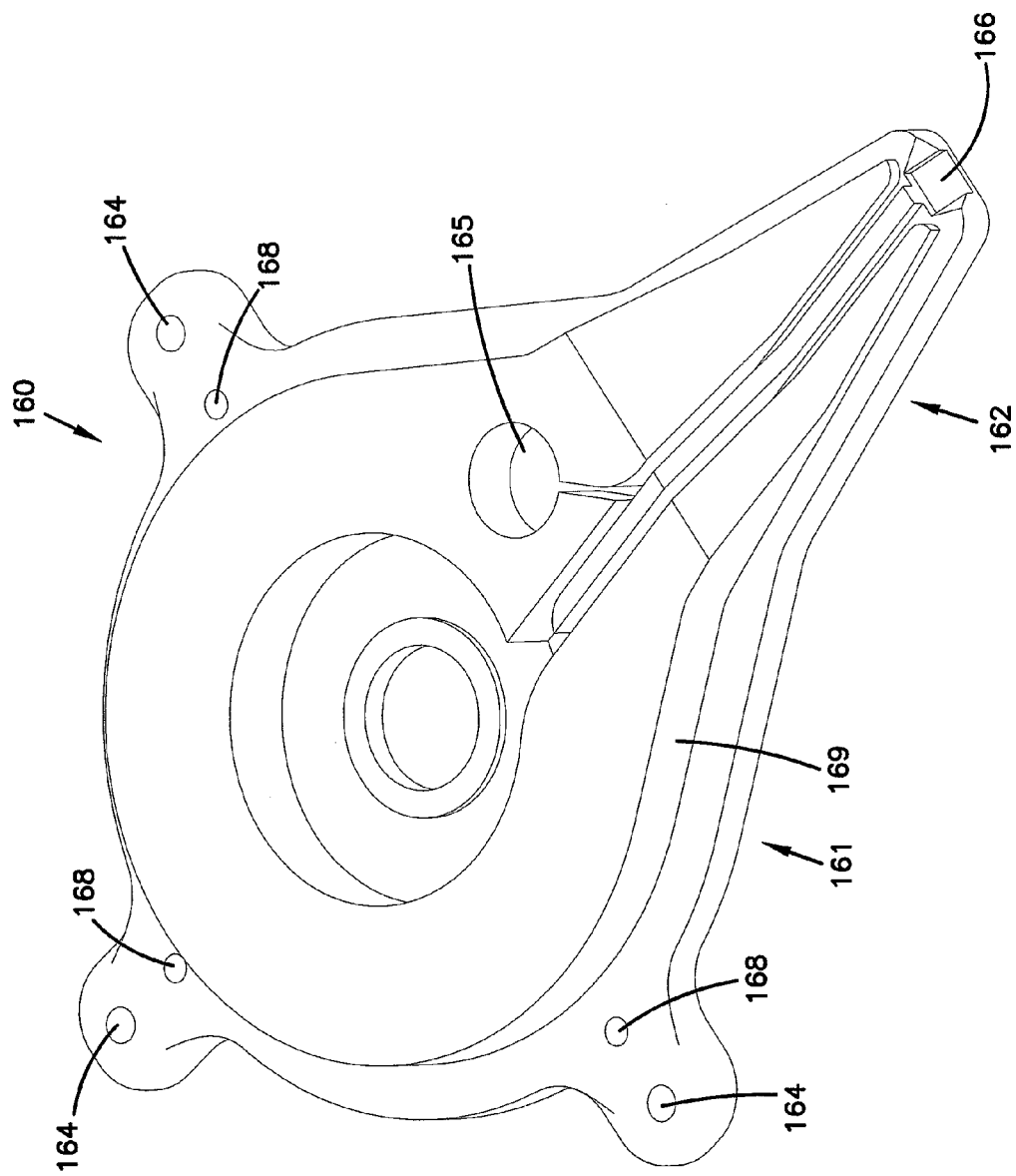
FIG. 9 is a top perspective view of an alternative embodiment of a base suitable for use with the tensioning apparatus of FIG. 2.

An alternative embodiment of a base 160 suitable for use with the tensioning apparatus 40 of FIG. 2 is illustrated in FIG. 9. The base 160 is similar to the base 60 of FIG. 4 except that base 160 includes certain additional features to those of the base 60.

Figure 10A:
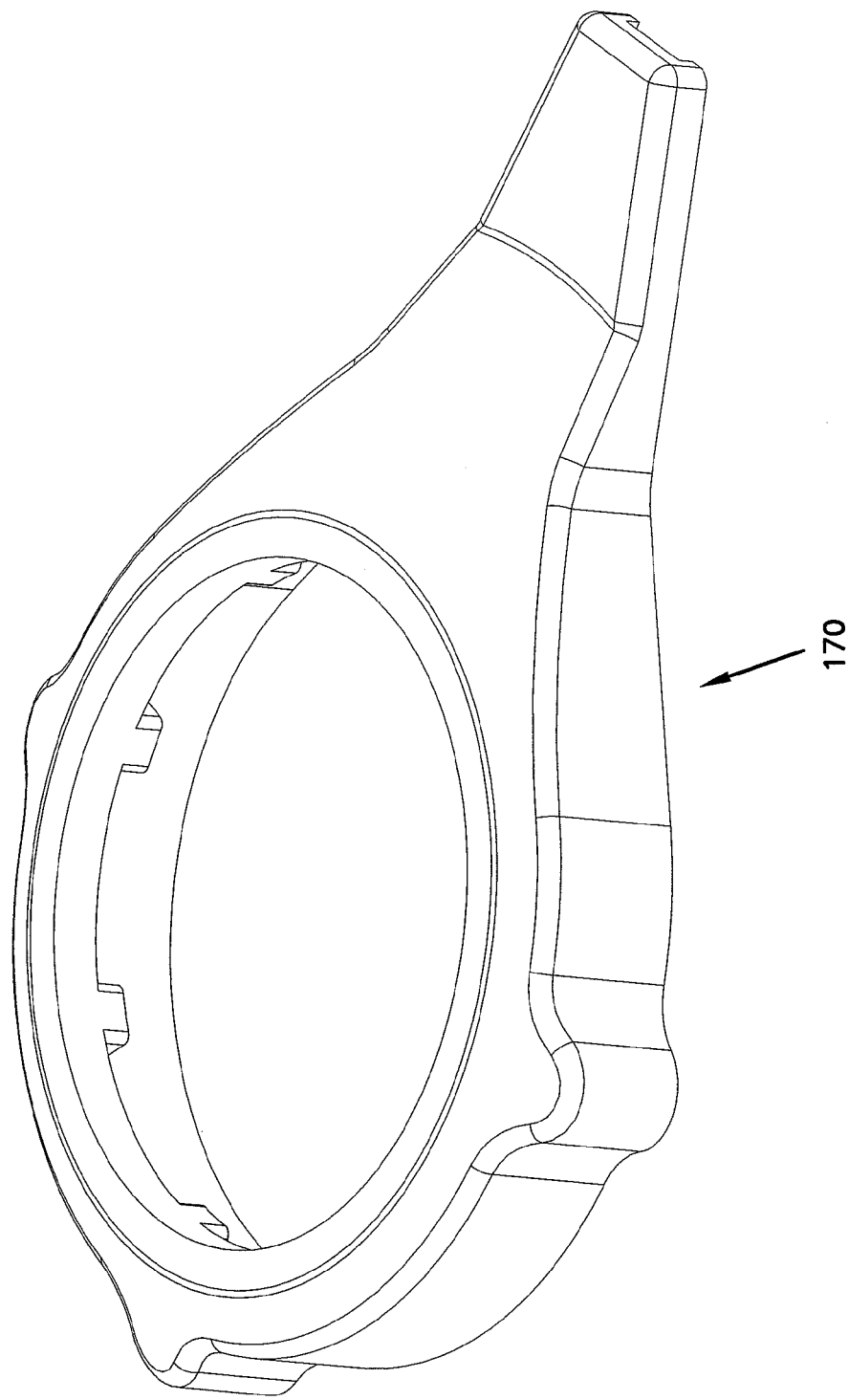
FIG. 10A is a top perspective view of an alternative embodiment of a cover suitable for use with the tensioning apparatus of FIG. 2.

First, base 160 includes fastener holes 168 adjacent the suture holes 164 defined on the three legs 163 disposed around the main body 161. The fastener holes 168 are configured to cooperate with the fastener holes 176 located in an alternative embodiment of the cover 170 that is depicted in FIGS. 10A and 10B.

Second, the base 160 includes an additional cavity 165 defined in the upper mounting portion 169 of the base 160. The cavity 165 may be used optionally to fixedly couple one end of the line 30 to the base 160 instead of winding both ends of the line 30 around the spool 80. After one end of the line 30 has been tied in a knot large enough so that it won't slip out of the cavity 165, that end can be placed into the cavity 165. In this manner, the biasing member provides tension on all the anchors 20 by pulling on only one end of the line 30 since the other end is fixedly supported by the base 160.

Figure 11:
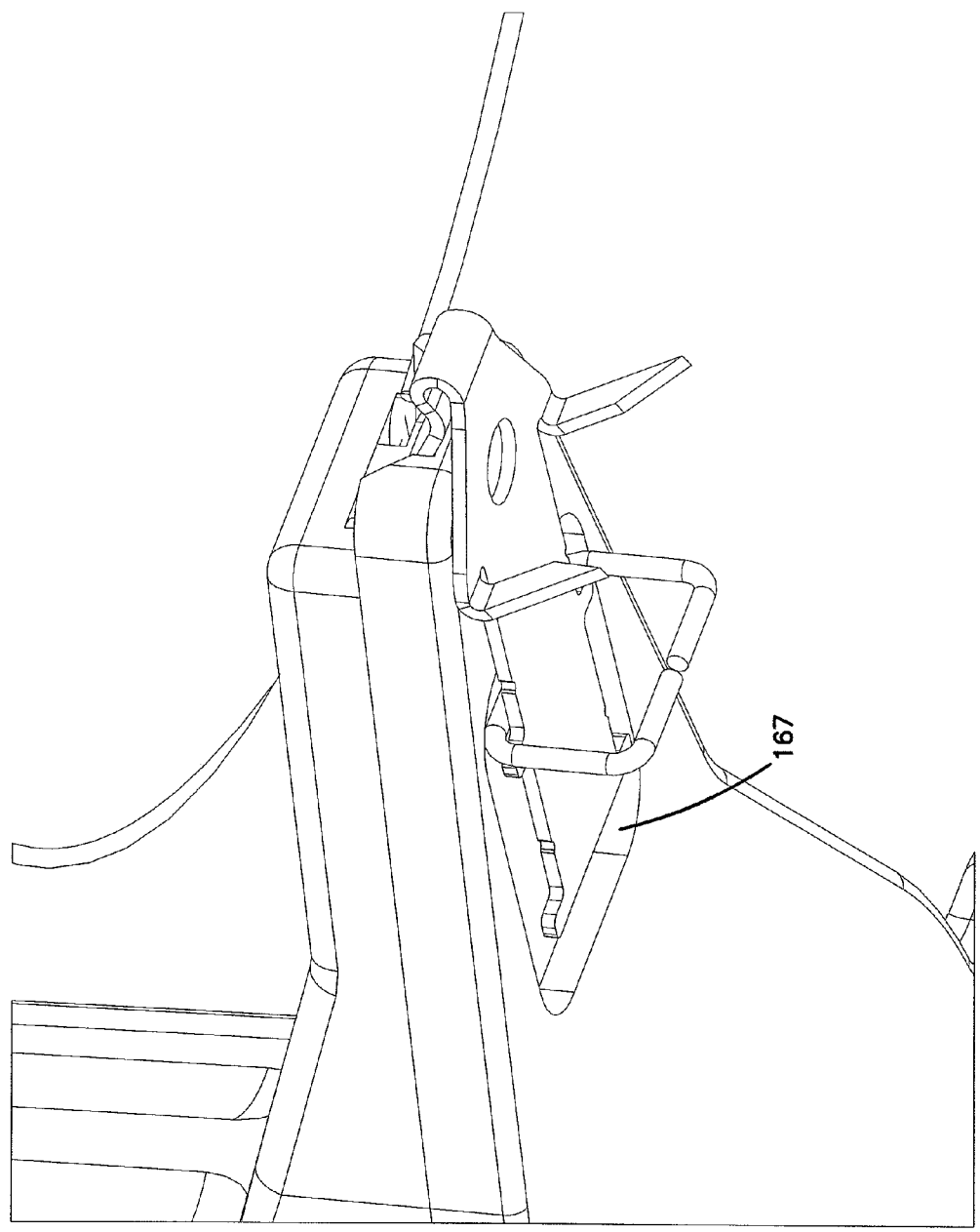
FIG. 11 is a partial bottom perspective view of the tensioning apparatus of FIG. 2, the tensioning apparatus including the alternative embodiment of the base of FIG. 9, the tensioning apparatus also shown attached to a skin anchor including similar features to the skin anchor of FIG. 8A and shown in combination with a tensioning line of the wound closure system of FIG. 1.

Third, the base 160 is provided with an extended snout portion 162 wherein the front of the snout 162 includes a ramped surface 166. The ramped surface 166 is configured to cooperate with the tension line tab 28 of a skin anchor 20 to fixedly mount the base 160 to a skin anchor. The ramped surface 166 is inserted within the tension line slot 29 defined by the tension line tab 28 of the skin anchor 20 as the tension line tab 28 abuts against the front of the snout 162. With this feature, the base 160 can be mounted onto an anchor 20 as seen in FIG. 11 and the tensioning apparatus can be allowed to move with the anchor 20 as the skin is stretched toward the wound 12. As illustrated in FIG. 11, since the snout portion 162 of the base 160 can be placed above the anchor 20 and can serve the function of an anchor, this embodiment of the base allows anchors 20 to be pulled in closer approximation to each other without the snout 162 taking up any space between the anchors 20. The base 160 is held coupled to the anchor 20 because the tension provided on the line 30 keeps the front of the snout 162 abutting against the tension line tab 28 of the skin anchor.

As illustrated in the bottom perspective view in FIG. 11, the bottom side of the base 160 may also include an indentation 167 configured to accommodate the thickness of a staple 22 mounted on top of the body 24 of an anchor 20.

2) Cover of Tensioning Apparatus

An alternative embodiment of a cover 170 suitable for use with the tensioning apparatus 40 of FIG. 2 is illustrated in FIGS. 10A and 10B. The cover 170 is similar to the cover 70 of FIGS. 7A and 7B except that cover 170 includes fastener holes 176 defined around the perimeter of the cover. The fastener holes 176 are adapted to cooperate with the fastener holes 168 of the base 160 of FIG. 9 to couple the cover 170 to the base 160 by means of fasteners (not shown in the FIGS.).

3) Skin Anchors

Figure 12A:
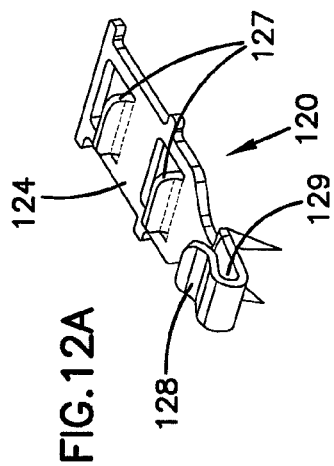
FIG. 12A is a top perspective view of an alternative embodiment of a skin anchor suitable for use with the wound closure system of FIG. 1.
Figure 12D:
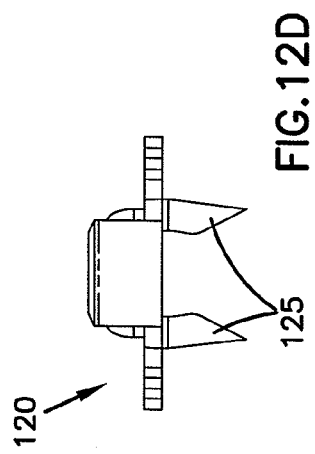
FIG. 12D is a front view of the skin anchor of FIG. 12A.
Figure 12B:
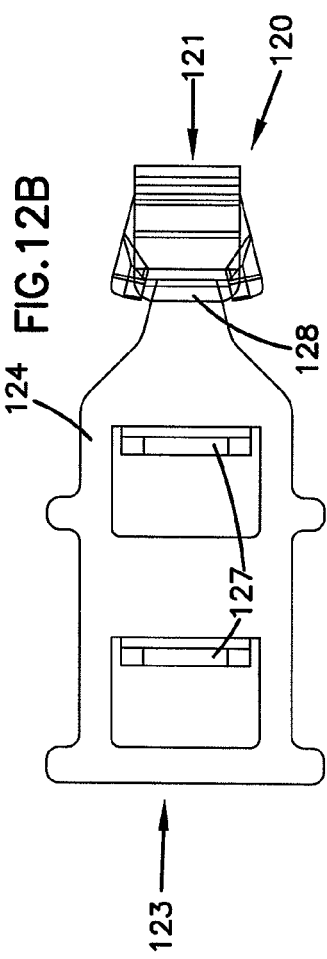
FIG. 12B is a top plan view of the skin anchor of FIG. 12A.
Figure 12C:
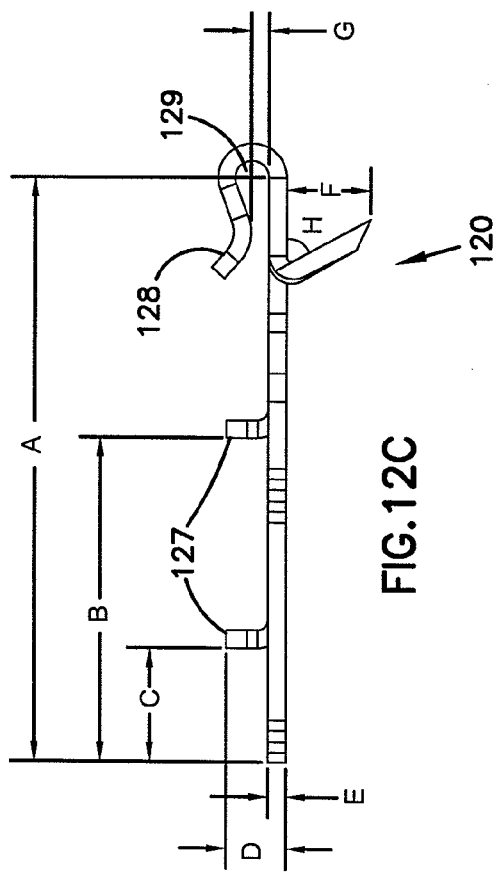
FIG. 12C is a side elevation view of the skin anchor of FIG. 12A.
Figure 12E:
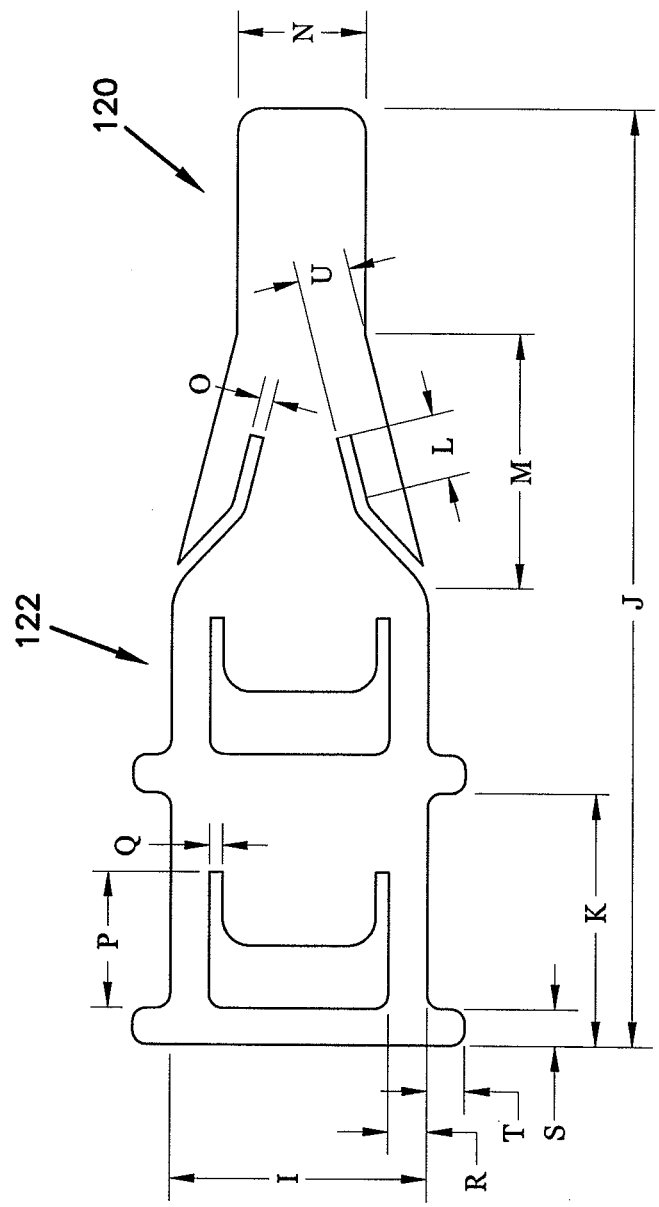
FIG. 12E is a top plan view of a plate from which the skin anchor of FIG. 12A is formed.

An alternative embodiment of an anchor 120 suitable for use with the wound closure system 10 of FIG. 1 is illustrated in FIGS. 12A-12E. In a preferred embodiment, the anchor 120 is formed from stainless steel such as 302 or 316 containing 8 to 14% nickel content. It can also be made from titanium. The stamped sheet 122 from which the anchor 120 is formed is illustrated in FIG. 12E in an unformed configuration.

The anchor 120 includes a first end 121 and a second end 123 and a generally rectangular body 124 defined between the first end 121 and the second end 123. The anchor 120 includes two skin-penetrating barbs 125 proximate the first end 121 for securement to the skin. The barbs 125 are flat on the bearing surface that pulls the skin closer over the wound. They are also bent at about a 60-degree angle to improve their ability to hold into the skin. The edges of the barbs 125 are sharpened to make it easy to penetrate the skin upon insertion. Two tabs 127 are formed on the body 124 to help guide where mechanical attachment, such as staples 22, are to be placed. A tension line tab 128 defines a tension line slot 129 formed at the first end 121 of the anchor 120 for receiving the tension line 30. The tension line tab 128 is formed with a wider lead-in to make it easy to receive the tension line 30 and then prevent the line from accidentally pulling out.

Anchor 120 includes dimensions A, B, C, D, E, F, G, H, I, J, K, L, M, N, O, P, Q, R, S, T, and U as seen in FIGS. 12C and 12E. The dimensions (A-U) can be varied according to desired skin anchor performance in different parts of the human body and for different types and ages of skin.

Table 2, below, illustrates three example configurations for the anchor 120, with three different sets of dimensions (A-U) that are suitable for use with the wound closure system 10. An anchor with example configuration 1 is preferably retained by two conventional regular size medical staples (5.7 mm×3.9 mm). Anchors with example configurations 2 and 3 are preferably retained by two wide size medical staples (6.9 mm×3.9 mm).

TABLE 2

Two-Barbed Anchors (unless otherwise specified, all dimensions are in inches)

| | A | B | C | D | E | F | G | H | I | J | K |
|---|---|---|---|---|---|---|---|---|---|---|---|
| Configuration 1 | 0.551 | 0.305 | 0.108 | 0.055 | 0.016 | 0.078 | 0.017 | 60° | 0.197 | 0.727 | 0.197 |
| Configuration 2 | 0.630 | 0.325 | 0.108 | 0.065 | 0.016 | 0.119 | 0.017 | 60° | 0.236 | 0.806 | 0.217 |
| Configuration 3 | 0.709 | 0.344 | 0.108 | 0.065 | 0.016 | 0.158 | 0.017 | 60° | 0.236 | 0.885 | 0.236 |

| | L | M | N | O | P | Q | R | S | T | U |
|---|---|---|---|---|---|---|---|---|---|---|
| Configuration 1 | 0.049 | 0.197 | 0.098 | 0.010 | 0.104 | 0.010 | 0.030 | 0.030 | 0.030 | 0.039 |
| Configuration 2 | 0.081 | 0.256 | 0.118 | 0.010 | 0.104 | 0.010 | 0.030 | 0.030 | 0.030 | 0.049 |
| Configuration 3 | 0.115 | 0.315 | 0.138 | 0.010 | 0.104 | 0.010 | 0.030 | 0.030 | 0.030 | 0.049 |

Figure 13A:
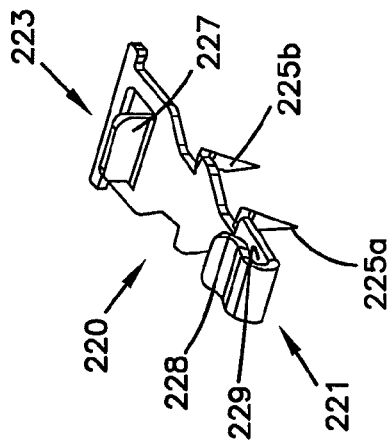
FIG. 13A is a top perspective view of a third embodiment of a skin anchor suitable for use with the wound closure system of FIG. 1.
Figure 13D:
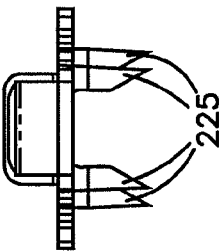
FIG. 13D is a front view of the skin anchor of FIG. 13A.
Figure 13B:
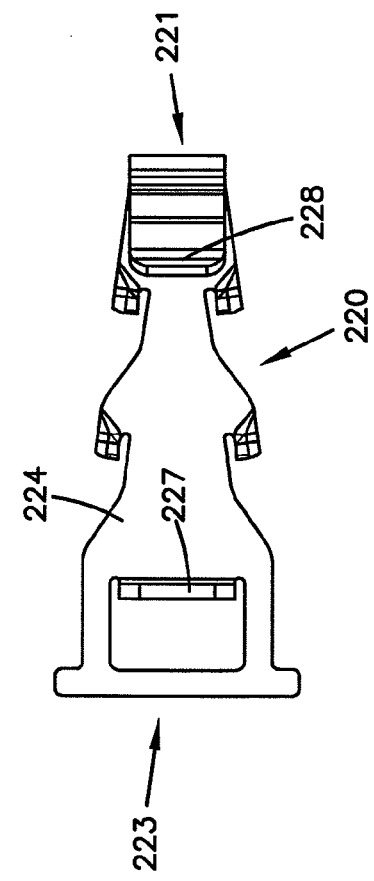
FIG. 13B is a top plan view of the skin anchor of FIG. 13A.
Figure 13C:
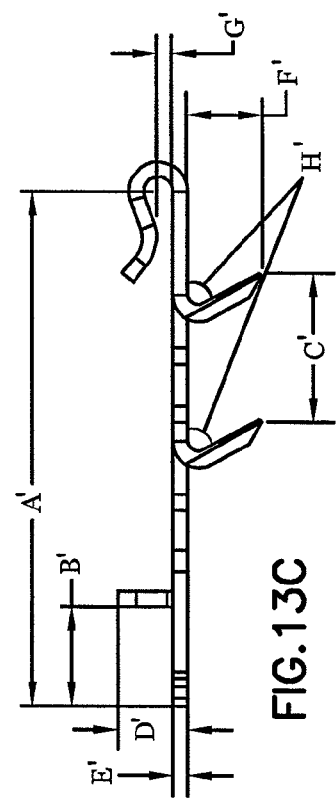
FIG. 13C is a side elevation view of the skin anchor of FIG. 13A.
Figure 13E:
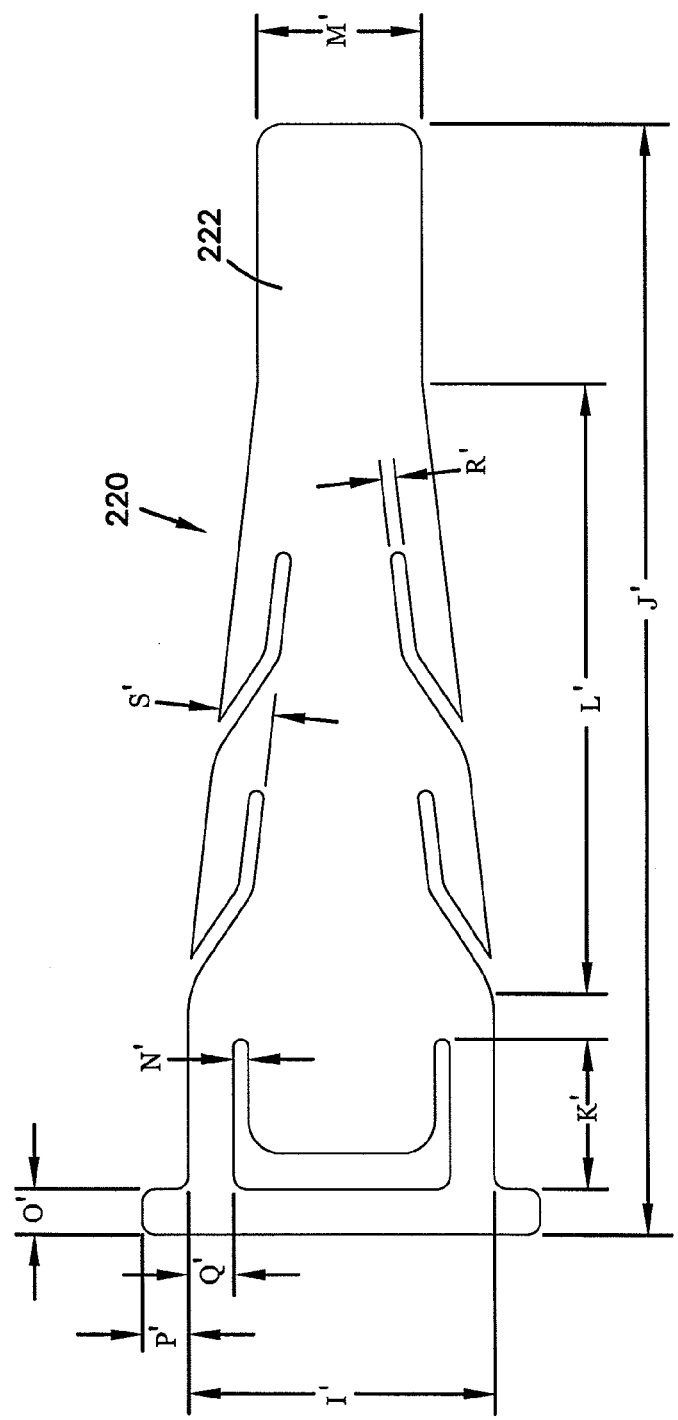
FIG. 13E is a top plan view of a plate from which the skin anchor of FIG. 13A is formed.

Another alternative embodiment of an anchor 220 is illustrated in FIGS. 13A-13E. The anchor 220 is also preferably formed from stainless steel such as 302 or 316 containing 8 to 14% nickel content. It can also be made from titanium. The stamped sheet 222 from which the anchor 220 is formed is illustrated in FIG. 13E. The anchor 220 is essentially similar to the anchor 120 except that the anchor 220 includes four skin-penetrating barbs 225 and one staple tab 227. Two of the barbs 225a are located proximate the first end 221 of the anchor 220 and two barbs 225b are located approximately halfway between the first end 221 and the second end 223 of the anchor 220. The tab 227 for guiding where the staples 22 are to be placed is formed adjacent the second end 223 of the anchor 220. Similar to anchor 120, a tension line tab 228 defines a tension line slot 229 formed at the first end 221 of the anchor 220 for receiving the tension line 30.

Anchor 220 includes dimensions A', B', C', D', E', F', G', H', I', J', K', L', M', N', O', P', Q', R', and S' as seen in FIGS. 13C and 13E. As for anchor 120, these dimensions (A'-S') can vary depending on the desired skin anchor performance in different parts of the human body and for different types and ages of skin.

Table 3, below, illustrates three example configurations for the anchor 220, with three different sets of dimensions (A'-S') that are suitable for use with the wound closure system 10. An anchor with example configuration 1 is preferably retained by one conventional regular size medical staple (5.7 mm×3.9 mm). Anchors with example configurations 2 and 3 are preferably retained by one wide size medical staple (6.9 mm×3.9 mm).

TABLE 3

Four-Barbed Anchors (unless otherwise specified, all dimensions are in inches)

| | A' | B' | C' | D' | E' | F' | G' | H' | I' | J' |
|---|---|---|---|---|---|---|---|---|---|---|
| Configuration 1 | 0.551 | 0.106 | 0.160 | 0.075 | 0.016 | 0.077 | 0.017 | 60° | 0.197 | 0.727 |
| Configuration 2 | 0.630 | 0.106 | 0.199 | 0.075 | 0.016 | 0.118 | 0.017 | 60° | 0.236 | 0.806 |
| Configuration 3 | 0.709 | 0.106 | 0.258 | 0.075 | 0.016 | 0.157 | 0.017 | 60° | 0.236 | 0.885 |

| | K' | L' | M' | N' | O' | P' | Q' | R' | S' |
|---|---|---|---|---|---|---|---|---|---|
| Configuration 1 | 0.098 | 0.394 | 0.098 | 0.010 | 0.030 | 0.030 | 0.030 | 0.010 | 0.034 |
| Configuration 2 | 0.098 | 0.472 | 0.118 | 0.010 | 0.030 | 0.030 | 0.030 | 0.010 | 0.039 |
| Configuration 3 | 0.098 | 0.571 | 0.138 | 0.010 | 0.030 | 0.030 | 0.030 | 0.010 | 0.049 |

FIGS. 14-19 illustrate six other embodiments of skin anchors 320-820, respectively, suitable for use with the wound closure system 10.

The skin anchor 320 of FIG. 14 includes a rectangular body 324 including a first end 321 and a second end 323. The body 324 includes two slots 327 for placement of staples 22, one located proximate the second end 323 and the other located between the two ends 321 and 323. The body 324 also defines a slot 329 adjacent the first end 321 for slidable placement of the tension line 30. Anchor 320 shown in FIG. 14 may be made of molded plastic.

The skin anchors 420 and 520 illustrated in FIGS. 15 and 16, respectively, are adapted to receive the tension line 30 from the underside of the body of the anchors prior to the anchors being attached to the skin. Anchors 620, 720, and 820 illustrated in FIGS. 17-19, respectively, include tension line tabs similar to anchors 20-220 and are adapted to receive the tension line 30 from the upper side of the body. Anchors 420-820, as illustrated in FIGS. 15-19, can be made in various ways such as from a plate, such as the plate 122 of FIG. 12E or 222 of FIG. 13E, from wire, by injection molding, or other suitable methods.

Figure 20:
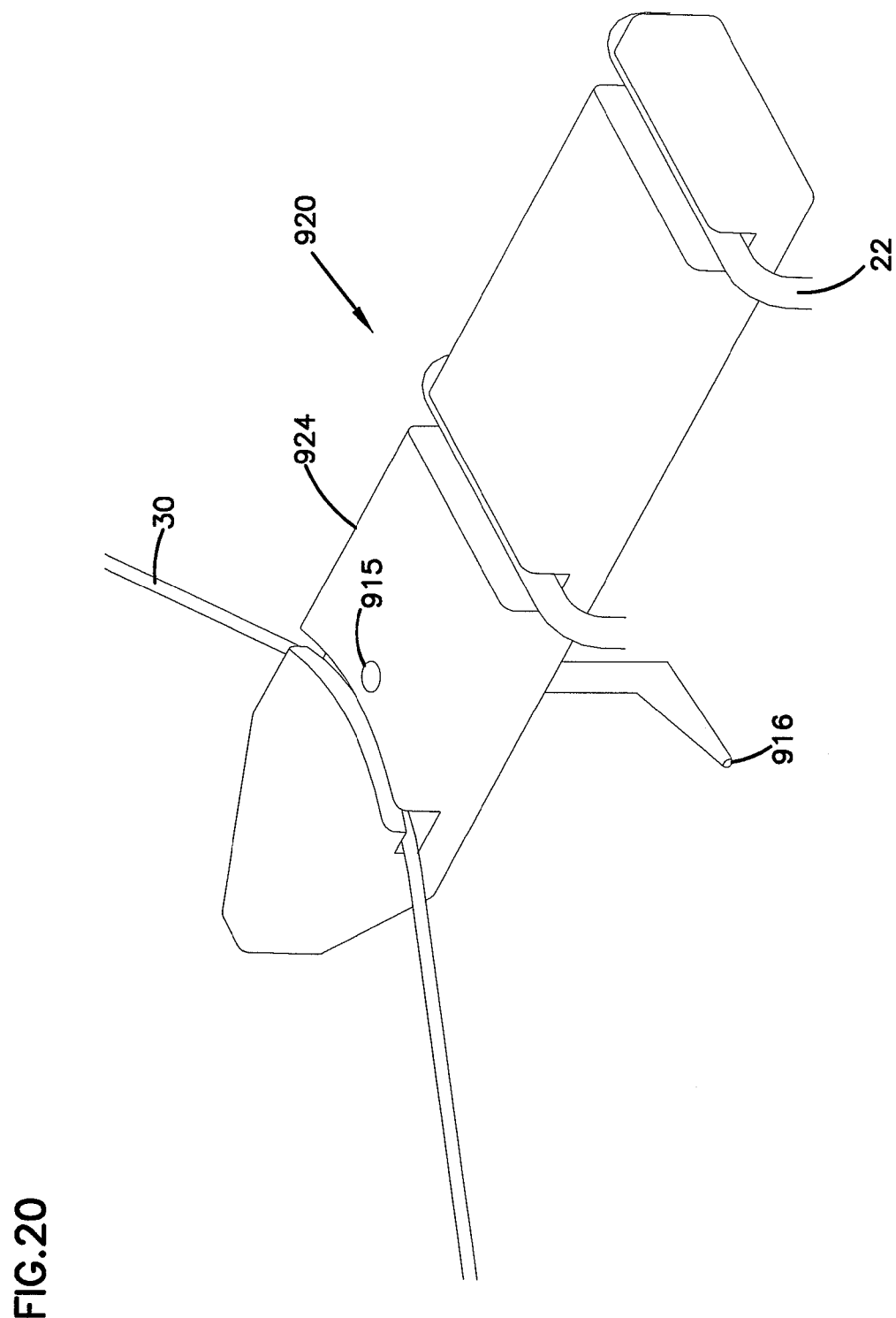
FIG. 20 is a perspective view of an tenth embodiment of a skin anchor suitable for use with the wound closure system of FIG. 1, the skin anchor including a hollow barb for oxygen delivery and shown in combination with a tensioning line of the wound closure system of FIG. 1 and shown attached to external skin tissue.

Referring to FIG. 20, another embodiment of a skin anchor 920 suitable for use with the wound closure system 10 is illustrated. Skin anchor 920 is shown in combination with the tensioning line 30 of the wound closure system 10 and shown attached to external skin tissue with staples 22. The skin anchor 920 is essentially similar to skin anchor 320 of FIG. 14 except that skin anchor 920 includes a barb 925 that is hollow. The anchor 920 includes a through hole 915 defined in the body 924 that runs through the hollow barb 925. The barb 925 also includes an exit hole 916 adapted to be exposed to the undersurface of the skin once the barb 925 penetrates the skin. The through hole 915 may be connected to an oxygen supply wherein oxygen is fed into the hollow barb 925 and out of the exit hole 916. In this manner, oxygen can be supplied around the wound area 12 through skin punctures that has been created by such skin anchors 920. It is known in the art that stretching of the skin tends to disrupt oxygen flow around the wound area. Exposing oxygen to a wound speeds up the healing and reduces the chance of infection by acting directly on anaerobic bacteria, enhancing leukocyte and macrophage activity and increasing the effects of antibiotics. The oxygen would be infused into the wound on a periodic basis to optimize wound healing and prevent over saturation with oxygen.

It will be understood that skin anchor 920 is only one example embodiment of an anchor that can be used to supply oxygen to the wound area. In certain embodiments, the body of the skin anchor might not include a throughhole and the oxygen supply can be directly linked to an entry hole on the barb of the skin anchor without the oxygen first passing through the body of the skin anchor. In such embodiments, the barb would include an entry hole exposed above the skin for attachment to an oxygen line and an exit hole disposed underneath the skin.

Although the anchors depicted in the figures are illustrated to have a generally rectangular body, it will be appreciated that other body shapes are also possible. A rectangular body may be utilized to accommodate the shape of conventional staples. The body of each anchor includes a longitudinal axis extending from the first end to the second end. The body of each anchor is preferably symmetrical about the longitudinal axis to equalize or improve pressure on the staples, the barbs or on any other method of attachment utilized for securement to skin.

4) Tensioning Apparatus

Figure 21:
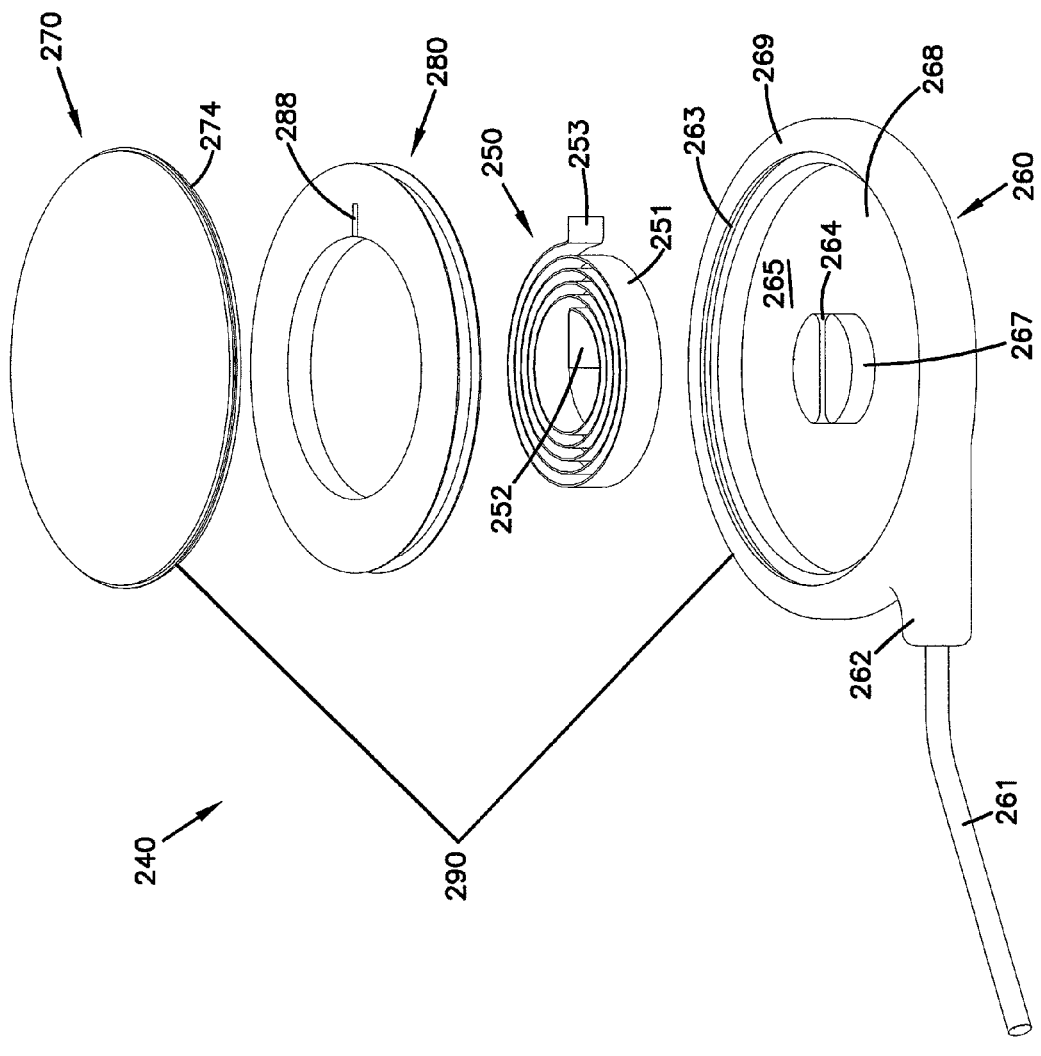
FIG. 21 is an exploded perspective view of an alternative embodiment of a tensioning apparatus suitable for use with the wound closure system of FIG. 1.

Referring to FIG. 21, an exploded perspective view of an alternative embodiment of a tensioning apparatus 240 suitable for use with the wound closure system 10 of FIG. 1 is illustrated therein. The tensioning apparatus 240 includes features similar to the tensioning apparatus 40 depicted in FIG. 1, however, operating in substantially a different manner in principle.

The tensioning apparatus 240 includes a housing 290 that is formed from a base 260 and a top cover 270. The housing 290 encloses a biasing member 250 and a spool member 280. Biasing member 250 provides the dynamic force for line 30, and spool member 280 collects and retains the portion of line 30 not being used.

The base 260 includes a generally circular interior cavity 265 for receiving the biasing member 250 and the spool member 280. The interior cavity 265 is defined by a bottom inner surface 268 and a surrounding periphery edge 269. An extended member 267 protrudes from the center of the bottom inner surface 268. The extended member 267 defines a slit 264 used for attachment of the biasing member 250, as will be described further below.

The top cover 270 is placed on top of the base 260 to securely enclose the biasing member 250 and the spool member 280 within the housing 290. In the embodiment of the tensioning apparatus 240, illustrated in FIG. 21, the periphery edge 269 and the top cover 270 define intermating threads 263 and 274, respectively, for removably coupling the top cover 270 to the base 260. It will be appreciated that other means of attachment between the top cover and the base are possible, such as snap fitting, friction fitting, twist-locking, etc. An exit port 262 is defined in the periphery edge 269 of the base 260.

The biasing member 250 is positioned within the interior cavity 265 of the base 260. The biasing member 250, as in the biasing member 50 of FIG. 1, is essentially formed from a coiled-up metal band 251. In a preferred embodiment, the band 251 is made of type 301 hi-yield stainless steel. In certain embodiments, the biasing member can provide a load force of about 4 lbs. In other embodiments, the amount of pulling force on the tension can be changed by changing the diameter of the tension line take up spool.

The band 251 defines an inner tab portion 252 and an outer tab portion 253. The biasing member 250 is positioned around the protruding extended member 267 of the base 260, so that inner tab portion 252 is received within the slit 264 to couple the biasing member to the base 260.

The spool member 280 is placed around the biasing member 250 within the base interior cavity 265. The spool member 280 defines a slit 288. The outer tab portion 253 is placed within the slit 288 to couple the biasing member 250 to the spool member 280.

With this configuration, when the spool member 280 is turned, the biasing member 250 is compressed or loaded. In the embodiment of the tensioning apparatus 240 illustrated in FIG. 21, turning the spool member 280 clockwise loads the biasing member 250 and turning it counterclockwise unloads the biasing member 250. It will be appreciated that, in other embodiments, an opposite orientation may be used.

The tension line 30 (shown in FIG. 1, but not in FIG. 21) is initially wound around the spool member 280 to set up the system. The tension line 30 is wound in such a manner as to not slip relative to the spool member 280 when pulled from an unwound end.

After the tension line 30 is wound around the spool member 280, pulling on the tension line 30 turns the spool member 280, which, in turn, loads the biasing member 250. The portion of the tension line 30 that will be attached to the anchors exits out of the exit port 262 of the housing 290.

A force guide tube 261, serving a similar function to the snout portion 62 of the base 60 of FIG. 4, positioned between tensioning apparatus 240 and the wound 12, provides a conduit through which line 30 passes. A force guide tube such as the one illustrated in FIG. 21 may also be used in the bases 60 and 160 of FIGS. 4 and 9, respectively, addition to the elongated snout portions of the bases 60 and 160. By providing structural support for the line 30, the force guide tube 261 allows the tensioning apparatus 240 to be positioned at a remote location from the wound 12. Remote placement of the tensioning apparatus 240 makes it easier to inspect and dress the wound 12. The force guide tube 261 also provides a way to concentrate the pulling forces into a single point rather than multiple points on the tensioning apparatus 240. The force guide tube 261 is depicted as coupled to the base 260 through the exit port 262. The force guide tube 261 may be coupled to the exit port 262 in various ways such as friction fitting, threading, adhesives, etc.

The force guide tube 261 is sized to have various lengths according to wound location and patient needs. In certain embodiments, the force guide tube may be integrally coupled to the tensioning apparatus or may be a removable part of the tensioning apparatus.

In a preferred embodiment, the tensioning apparatus 240 may also include a tension drag mechanism (not shown in the FIGS.). The tension drag mechanism may be an integral part of the base 260. The tension drag mechanism may include a drag knob that can be activated to stop or reduce the pulling force of the biasing member 250. In one embodiment, the tension drag mechanism may include an on/off type mechanism. In such an embodiment, pressing the drag knob applies enough friction on the biasing member 250 to cause it to stop pulling. In a preferred embodiment, the tension drag mechanism is constructed to apply varying degrees of drag or friction on the biasing member 250. In this way, the tension drag knob can be activated to stop the pulling force and, then, released gradually to allow the biasing member 250 to apply tension gradually. Gradual release prevents the biasing member 250 from applying full tension immediately after being released, which can be painful for the patient.

The tension drag mechanism can be used when first setting up the wound closure system 10 around the wound 12 or during readjustment of the system. In use of the tension drag mechanism, the tension line 30 can be pulled from the tensioning apparatus 240 and the tension drag knob can be activated to temporarily stop the pulling force of the biasing member 250. When the tension line 30 is placed around the anchors, the tension drag knob can be released to allow biasing member 250 to start applying a tension force again.

The tensioning apparatus 240 can either be located near the wound area 12 or away from the wound area 12 if a force guide tube 261 is used. In certain embodiments, the tensioning apparatus 240 can be secured to the patient by surface attachment, such as by adhesive, adhesive tape, a bandage, or wound dressing. In other embodiments, the tensioning apparatus can be located outside of a patient's body.

5) Alternative Use of Wound Closure System

The wound closure system may be used to stretch the skin for purposes other than for wound closure. One such example use of the wound closure system is directed to improving the cosmetic effects of male-pattern baldness. For example, the skin anchors may be placed on the human scalp around the periphery of the so called "bald-spot." The tensioning apparatus or an elastic tension line, for example, then, may be used to gradually draw the skin anchors inwardly to stretch the skin with the hair follicles surrounding the bald-spot to eventually reduce the size of the bald-spot.

G. Negative Pressure Wound Dressing Apparatus

Figure 22:
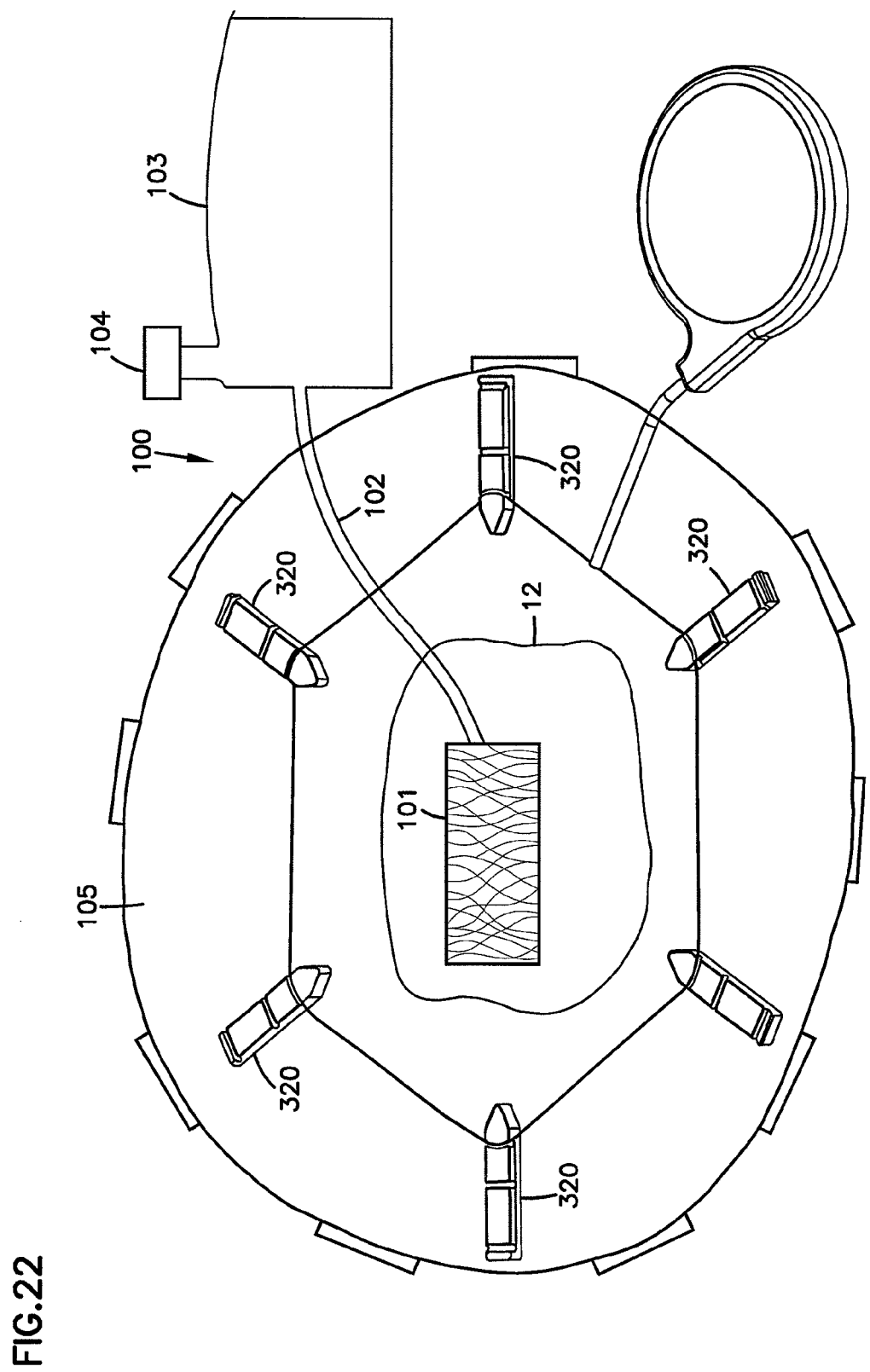
FIG. 22 is a diagrammatic view of a negative pressure wound dressing apparatus suitable for use with the wound closure system of FIG. 1, shown in combination with a wound closure system including the tensioning apparatus of FIG. 21 and skin anchors with features similar to the skin anchor of FIG. 14.

Referring to FIG. 22, there is illustrated therein a diagrammatic view of a negative pressure wound dressing apparatus 100 adapted to be used in conjunction with the wound closure system 10. Although depicted as being used in combination with a wound closure system that includes the alternative embodiment of the tensioning apparatus of FIG. 21 and skin anchors with features similar to the skin anchor 320 of FIG. 14, the negative pressure wound dressing apparatus 100 may also be used with the wound closure system 10 depicted in FIG. 1.

The negative pressure wound dressing apparatus 100 includes a filter pad 101 that is adapted to be placed in or over the wound 12. A drain tube 102 extends from the filter pad 101 to a pressure vessel such as squeeze bulb 103. The squeeze bulb 103 includes an interior volume for holding liquids. The squeeze bulb 103 also includes a drain cap 104 that is removably coupled to the squeeze bulb 103 for emptying the bulb. It will be appreciated that the drain cap 104 can be coupled the squeeze bulb 103 in a number of different ways such as with threads, by snap-fitting, etc.

In general use, the filter pad 101 is placed in the wound 12. The squeeze bulb 103 is squeezed by the user to create a negative pressure in the filter pad 101. The negative pressure then soaks up any excess fluid there may be in the wound area 12 and helps pull the wound closed. As the squeeze bulb 103 is filled with excess drainage from the wound area 12, it can be emptied through the drain cap 104. Preferably, the squeeze bulb 103 is squeezed two or three times a day by the user. In other embodiments, the negative pressure wound dressing apparatus 100 may be constructed such that the squeeze bulb 103 is compressed automatically. For example, the squeeze bulb 103 may be attached to a person's body in such a manner as to be compressed each time the person breathes. In other embodiments, the squeeze bulb 103 may be squeezed automatically by other bodily movements such as the movement of a person's leg or arm. Body movement might also be used in conjunction with piezo-electric materials to generate power to operate the negative pressure mechanism.

As shown in FIG. 22, a cover 105 that covers the entire wound area 12 and the skin anchors 320, may be placed on the skin so that suction through the filter pad 101 is more effective by creating an internal vacuum around the wound area 12. Preferably, the cover 105 is impermeable to liquid and to air. Plastic is a suitable material for cover 105. The cover 105 may be attached to the skin around the perimeter of the wound 12 by adhesives or other suitable methods.

From the foregoing detailed description, it will be evident that modifications and variations can be made in the devices of the invention without departing from the spirit or scope of the invention. Therefore, it is intended that all modifications and variations not departing from the spirit of the invention come within the scope of the claims and their equivalents.

We claim:

1. A wound closure system comprising:
   (a) a plurality of skin anchors adapted to be attached to external skin tissue around a periphery of a wound;
   (b) a line adapted to extend between each of the skin anchors without any portion of the line penetrating through the skin tissue; and
   (c) a tensioning member that is separate from the line that is adapted to apply a pulling force on the line to draw all of the skin anchors toward each other, wherein no portion of the tensioning member is located inside the periphery of the wound when the wound closure system is set up, the tensioning member adapted to apply a pulling force on the line to keep the line taut between the skin anchors as the skin anchors move toward each other, wherein each skin anchor includes a tab defining a slot for receiving a portion of the line that extends between each of the skin anchors, wherein the line is configured to slide within the slot with respect to the tab as the skin anchors move toward each other, and wherein the tensioning member that is separate from the line defines a portion configured to engage the tab of one of the skin anchors for coupling the tensioning member to the skin anchor to allow for movement of the tensioning member with the skin anchor.

2. A wound closure system according to claim 1, wherein the line is adapted to extend around substantially the entire periphery of the wound.

3. A wound closure system according to claim 1, wherein at least one of the anchors is adapted to be attached to external skin tissue with a skin-penetrating structure.

4. A wound closure system according to claim 1, wherein the plurality of skin anchors includes at least three or more skin anchors.

5. A wound closure system according to claim 1, wherein the tensioning member includes a spring for applying an automatic continuous pulling force on the line to keep the line taut between the skin anchors as the skin anchors move toward each other.

6. A wound closure system according to claim 5, further comprising a housing that houses the spring, the housing including a spool rotatably coupled to the housing, the spool coupled to the spring and adapted for winding the spring for the application of the continuous pulling force on the line, the housing and the spring including intermating structures adapted for winding the spring, wherein the intermating structures are adapted to slip with respect to each other when the spring has been fully wound to provide an indication that the spring is fully wound.

7. A wound closure system according to claim 6, wherein the intermating structures include radially arranged indents formed within the housing and a radially outwardly protruding tab of the spring.

8. A wound closure system comprising:
(a) a plurality of skin anchors adapted to be attached to external skin tissue around a periphery of a wound;
(b) a line adapted to extend between each of the skin anchors without any portion of the line penetrating through the skin tissue, the line adapted to extend between the skin anchors in a shoe-lace configuration wherein the line includes a portion that is adapted to cross the wound at least twice when the wound closure system is set up; and
(c) a tensioning member that is separate from the line that is adapted to apply a pulling force on the line to draw all of the skin anchors toward each other, wherein no portion of the tensioning member is located inside the periphery of the wound when the wound closure system is set up, the tensioning member adapted to apply a pulling force on the line to keep the line taut between the skin anchors as the skin anchors move toward each other, wherein each skin anchor includes a tab defining a slot for receiving a portion of the line that extends between each of the skin anchors, wherein the line is configured to slide within the slot with respect to the tab as the skin anchors move toward each other, and wherein the tensioning member that is separate from the line defines a portion configured to engage the tab of one of the skin anchors for coupling the tensioning member to the skin anchor to allow for movement of the tensioning member with the skin anchor.

9. A wound closure system according to claim 8, wherein at least one of the anchors is adapted to be attached to external skin tissue with a skin-penetrating structure.

10. A wound closure system according to claim 8, wherein the plurality of skin anchors includes at least three or more skin anchors.

11. A wound closure system according to claim 8, wherein the tensioning member includes a spring for applying an automatic continuous pulling force on the line to keep the line taut between the skin anchors as the skin anchors move toward each other.

12. A wound closure system according to claim 11, further comprising a housing that houses the spring, the housing including a spool rotatably coupled to the housing, the spool coupled to the spring and adapted for winding the spring for the application of the continuous pulling force on the line, the housing and the spring including intermating structures adapted for winding the spring, wherein the intermating structures are adapted to slip with respect to each other when the spring has been fully wound to provide an indication that the spring is fully wound.

13. A wound closure system according to claim 12, wherein the intermating structures include radially arranged indents formed within the housing and a radially outwardly protruding tab of the spring.

14. A method of closing a wound, the method comprising the steps of:
(a) attaching a plurality of skin anchors to external skin tissue around a periphery of a wound;
(b) extending a line between each of the skin anchors without any portion of the line penetrating through the skin tissue;
(c) providing a tensioning member that is separate from the line that is adapted to apply a pulling force on the line to draw all of the skin anchors toward each other, wherein no portion of the tensioning member is located inside the periphery of the wound when the wound closure system is set up, the tensioning member adapted to apply a pulling force on the line to keep the line taut between the skin anchors as skin anchors move toward each other, wherein each skin anchor includes a tab defining a slot for receiving a portion of the line that extends between each of the skin anchors, wherein the line is configured to slide within the slot with respect to the tab as the skin anchors move toward each other; and
(d) engaging the tab of one of the skin anchors with a portion of the tensioning member that is separate from the line for coupling the tensioning member to the skin anchor to allow for movement of the tensioning member with the skin anchor.

15. A method according to claim 14, further comprising extending the line around substantially the entire periphery of the wound.

16. A method according to claim 14, further comprising attaching at least one of the skin anchors to external skin tissue with a skin-penetrating structure.

17. A method according to claim 14, wherein the plurality of skin anchors includes at least three or more skin anchors.

18. A method according to claim 14, wherein the tensioning member includes a spring for applying an automatic continuous pulling force on the line to keep the line taut between the skin anchors as the skin anchors move toward each other.

19. A method according to claim 18, further comprising providing a housing that houses the spring, the housing including a spool rotatably coupled to the housing, the spool coupled to the spring and adapted for winding the spring for the application of the continuous pulling force on the line, the housing and the spring including intermating structures adapted for winding the spring, wherein the intermating structures are adapted to slip with respect to each other when the spring has been fully wound to provide an indication that the spring is fully wound.

20. A method according to claim 19, wherein the intermating structures include radially arranged indents formed within the housing and a radially outwardly protruding tab of the spring.

* * * * *